US009804152B1

(12) United States Patent
Finlay et al.

(10) Patent No.: US 9,804,152 B1
(45) Date of Patent: Oct. 31, 2017

(54) HUMAN EX VIVO SKIN MODEL AND ITS USE IN METHODS OF IDENTIFYING MODULATORS OF SKIN INFLAMMATION

(71) Applicant: The Procter & Gamble Company, Cincinnati, OH (US)

(72) Inventors: Deborah Ruth Finlay, Cincinnati, OH (US); Kevin John Mills, Goshen, OH (US); Charles Carson Bascom, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 270 days.

(21) Appl. No.: 13/967,887

(22) Filed: Aug. 15, 2013

Related U.S. Application Data

(60) Provisional application No. 61/683,452, filed on Aug. 15, 2012.

(51) Int. Cl.
*G01N 33/50* (2006.01)
*G01N 33/68* (2006.01)
*A61K 38/19* (2006.01)

(52) U.S. Cl.
CPC ......... *G01N 33/5088* (2013.01); *A61K 38/19* (2013.01); *G01N 33/5008* (2013.01); *G01N 33/5023* (2013.01); *G01N 33/5044* (2013.01); *G01N 33/6869* (2013.01); *G01N 33/6881* (2013.01); *C12Q 2600/136* (2013.01); *C12Q 2600/148* (2013.01); *C12Q 2600/158* (2013.01); *G01N 2333/545* (2013.01); *G01N 2500/10* (2013.01); *G01N 2800/20* (2013.01); *G01N 2800/202* (2013.01)

(58) Field of Classification Search
CPC ........ C12Q 2600/158; C12Q 2600/136; C12Q 2600/148; G01N 33/5088; G01N 33/6869; G01N 33/6881; G01N 33/5044; G01N 2322/545; G01N 2500/10; G01N 2800/20; G01N 2800/202; G01N 33/5008; A71K 38/19
See application file for complete search history.

(56) References Cited

U.S. PATENT DOCUMENTS

| 2,694,668 | A | 11/1954 | Fricke |
|---|---|---|---|
| 2,809,971 | A | 10/1957 | Bernstein |
| 2,826,551 | A | 3/1958 | Geen |
| 3,152,046 | A | 10/1964 | Kapral |
| 3,236,733 | A | 2/1966 | Karsten |
| 3,753,196 | A | 8/1973 | Kurtz |
| 3,755,560 | A | 8/1973 | Dickert et al. |
| 3,761,418 | A | 9/1973 | Parran, Jr. |
| 3,964,500 | A | 6/1976 | Drakoff |
| 4,323,683 | A | 4/1982 | Bolich, Jr. |
| 4,345,080 | A | 8/1982 | Bolich, Jr. |
| 4,364,837 | A | 12/1982 | Pader |
| 4,379,753 | A | 4/1983 | Bolich, Jr. |
| 4,421,769 | A | 12/1983 | Dixon |
| 4,470,982 | A | 9/1984 | Winkler |
| 4,677,120 | A | 6/1987 | Parish et al. |
| 4,741,855 | A | 5/1988 | Grote |
| 4,885,107 | A | 12/1989 | Wetzel |
| 4,885,311 | A | 12/1989 | Parish et al. |
| 5,049,584 | A | 9/1991 | Purcell et al. |
| 5,104,646 | A | 4/1992 | Bolich, Jr. |
| 5,106,609 | A | 4/1992 | Bolich, Jr. |
| 5,124,356 | A | 6/1992 | Purcell et al. |
| RE34,075 | E | 9/1992 | Purcell et al. |
| RE34,584 | E | 4/1994 | Grote |
| 5,624,666 | A | 4/1997 | Coffindaffer |
| D391,162 | S | 2/1998 | Kokenge |
| 6,451,300 | B1 | 9/2002 | Dunlop |
| 6,974,569 | B2 | 12/2005 | Dunlop |
| 7,001,594 | B1 | 2/2006 | Peffly |
| D516,436 | S | 3/2006 | Campbell |
| 7,101,889 | B2 | 9/2006 | Kaczvinsky |
| D535,191 | S | 1/2007 | Corker |
| D542,660 | S | 5/2007 | Thomas |
| D547,193 | S | 7/2007 | Blasko |
| D547,661 | S | 7/2007 | Blasko |
| D558,591 | S | 1/2008 | Blasko |
| D563,221 | S | 3/2008 | Ashiwa |
| D570,707 | S | 6/2008 | Blasko |

(Continued)

FOREIGN PATENT DOCUMENTS

| EP | 2019316 | 1/2009 |
|---|---|---|
| GB | 849433 A | 9/1960 |

(Continued)

OTHER PUBLICATIONS

Guilloteau, K., et al. Skin inflammation induced by the synergistic action of IL-17A, IL-22, Oncostatin M, IL-1alpha, and TNF-alpha recapitulates some features of psoriasis. J. Immunol., 2010, vol. 184, p. 5263-5270.*
Zhang X, et al. Simvastatin inhibits IL-17 secretion by targeting multiple IL-17-regulatory cytokines and by inhibiting the expression of IL-17 transcription factor RORC in CD4+ lymphocytes. J. Immunol., 2008, vol. 180, p. 6988-6996.*
"Genomics of Skin Aging: Practical Applications", Journal of Drugs in Dermatology Supplement, vol. 8, Issue 7 (2009).
Bissett el al. "Niacinamide: A B Vitamin that Improves Aging Facial Skin Appearance" American Society for Dermatologic Surgery Inc., Dermatol Surg 2005; 31:860-865.
In Vitro Biomarker Responses to a New Anti-Aging Peptide, PAL-KT, Osborne et al, American Academy of Dermatology 67th Annual Meeting Media Resources, 2009.

(Continued)

*Primary Examiner* — Robert Landsman
*Assistant Examiner* — Bruce D Hissong
(74) *Attorney, Agent, or Firm* — John G. Powell

(57) ABSTRACT

Provided are methods and systems for determining functional relationships between ex vivo skin models and an inflammatory skin condition. Also provided are methods and systems for identifying modulators of inflammation of skin, as well as the use of modulators identified by such methods or systems for the preparation of cosmetic compositions, personal care products, or both.

19 Claims, 8 Drawing Sheets

(56) References Cited

U.S. PATENT DOCUMENTS

| | | | |
|---|---|---|---|
| 7,531,497 | B2 | 5/2009 | Midha |
| 7,585,827 | B2 | 9/2009 | Geary |
| 7,654,420 | B2 | 2/2010 | Honda |
| 7,704,932 | B2 | 4/2010 | Evans |
| 7,709,015 | B2 | 5/2010 | Masuda |
| 7,727,516 | B2 | 6/2010 | Botchkareva |
| 7,772,214 | B2 | 8/2010 | Vatter |
| 8,324,447 | B2 | 12/2012 | Goldstein |
| 2003/0223951 | A1 | 12/2003 | Geary |
| 2007/0040306 | A1 | 2/2007 | Morel |
| 2007/0205226 | A1 | 9/2007 | Honda et al. |
| 2007/0254021 | A1* | 11/2007 | Scimeca ............ A61K 8/0208 424/450 |
| 2009/0017080 | A1 | 1/2009 | Tanner |
| 2009/0064349 | A1 | 3/2009 | Goldstein |
| 2009/0110709 | A1 | 4/2009 | Mitts |
| 2009/0298113 | A1 | 12/2009 | Vielhaber |
| 2011/0150798 | A1 | 6/2011 | Bacus |
| 2011/0269852 | A1 | 11/2011 | McDaniel |
| 2012/0283112 | A1 | 11/2012 | Binder |
| 2013/0337087 | A1 | 12/2013 | Finlay |
| 2014/0335532 | A1 | 11/2014 | Finlay |
| 2015/0004616 | A1 | 1/2015 | Finlay |

FOREIGN PATENT DOCUMENTS

| | | |
|---|---|---|
| WO | WO 2011/087523 | 1/2011 |
| WO | 2012011904 A1 | 1/2012 |
| WO | 2012116081 A2 | 8/2012 |
| WO | WO2013192076 | 12/2013 |
| WO | WO2014028569 | 2/2014 |
| WO | WO2014028572 | 2/2014 |

OTHER PUBLICATIONS

Skin Biomarkers Confirm the Anti-Oxidant Activity of Olive Derivatives and Yeast Ferment Filtrate, Finlay et al., P&G 67th Annual Meeting of American Academy of Dermatology (2009).

Jensen, et al. "Acid and neutral sphingomyelinase, cermide synthase, and acid ceramidase activities in cutaneous aging" Experimental Dermatology 2005p.609-616.

Pels, et al. "Clobetasol Propionate—Where, When, Why?", Drugs of Today 2008, 44(7): 547-557.

Tjabringa, G et al. "Development and Validation of Human Psoriatic Skin Equivalents"; The American Journal of Pathology, vol. 173, No. 3, Sep. 2008, 9 pps.

Arsic, I, et al. "Preparation of Novel Apigenin-Enriched, Liposomal and Non-Liposomal, Antiinflammatory Topical Formulations as Substitutes for Corticosteroid Therapy" Phytotherapy Research, 25: 228-233 (2011), 6 pps.

Hegyi, A. et al. "Vitamin D Analog Calcipotriol Suppresses the Th17 Cytokine-Induced Proinflammatory S100 "Alarmins" Psoriasin (S100A7) and Koebnerisin *S100A15 in Psoriasis" Journal of Investigative Dermatology 2012, vol. 132, 9 pages.

International Search Report; PCT/US2013/055138, dated Nov. 12, 2013; 15 pages.

Millikin, Cheri et al. "Topical N-acetyl glucosamine and niacinamide affect pigmentation relevant gene expression in in vitro geonomics experimentation" Journal American Acadamy of Dermatology, Feb. 2007.

Bissett, Donald, et al. "Genomic Expression Changes Induced by Topical N-acetyl Glucosamine in Skin Equivalent Cultures in Vitro" Journal of Cosmetic Dermatology.

Yumiko, I., et al. "Identification of Novel Hair-Growth Inducers by means of Connectivity Mapping", FASEB Journal, vol. 24, May 2010.

Hughes, T.R. et al. "Functional discovery via a compendium of expression profiles" Cell vol. 102, 109-126 (2000).

Jagetia G. C. et al, "Genotoxic Effect of Hydroquinone on the Cultured Mouse Spleenocytes" Toxicology Letter 121(1):15-20, 2001.

Lamb, Justin, et al. "Connectivity Map: Gene Expression Signatures to Connect Small Molecules, Genes, and Disease", Science, vol. 313, 2006.

M. Hollander et al. "Nonparametric Statistical Methods"; Wiley, New York, ed. 2, 1999 see, e.g., pp. 178-185.

Raynaud E. et al., "Depigmentation for cosmetic purposes: prevalence and side-effects in a female population in Senegal" Ann Dermatol Venereol 128(6-7):720-724, 2001 (abstract).

Shimizu K. et al., "The skin-lightening effects of artocarpin on UVB-induced pigmentation "Planta Med 68(1):79-81, 2002.

Sivapirabu, G. et al., "Topical Nicotinamide Modulates Cellular Energy Metabolism and Provides Broad-Spectrum Protection Against Ultraviolet Radiation-Induced Immunosuppression in Humans", British Journal of Dermatology 2009.

Subramanian A. et al, Gene set enrichment analysis: A knowledge-based approach for interpreting genome-wide expression profiles. (2005) Proc.Natl.Acad Sci U.S.A, 102, 15545-15550.

International Search Report; PCT/US2013/034055; dated Jun. 11, 2013; 17 pages.

International Search Report PCT/US2013/034052; dated Jun. 11, 2013; 18 pages.

International Search Report PCT/US2013/034054; dated Jun. 13, 2013; 18 pages.

International Search Report PCT/US2013/034055; dated Jun. 11, 2013; 17 pages.

International Search Report PCT/US2013/034117; dated Jun. 11, 2013; 17 pages.

Johnson, "Skin conditions and related need for medical care amount persons 1-74 years, United States, 1971-1974." Vital and Health Statistics, Series 11, No. 212, DHEW publication No. (PHS) 79-1660, U.S. Department of Health, Education and Welfare, National Center for Health Statistics 1978: 1-72.

Smith et al.,"The effect of a high-protein, low glycemic—load diet versus a conventional, high glycemic-load diet on biochemical parameters associated with acne vulgaris: A randomized, investigator-masked, controlled trial" Journal of the American Academy of Dermatology vol. 57 (2): 247-56 (2007).

Kluken et al., "Atopic eczema/dermatitis syndrome—a genetically complex disease. New advances in discovering the genetic contribution" Allergy, 58(1):5-12 (2003).

Cork et al., "Epidermal barrier dysfunction in atopic dermatitis" J Invest Dermatol., 129(8):1892-908 (2009).

Kimata et al., "Enhancement of Allergic Skin Wheal Responses by Microwave Radiation from Mobile Phones in Patients with Atopic Eczema/Dermatitis Syndrome" Int Arch of Allergy and Immunology, 129 (4):348-350 (2002).

Wang et al., "Environmental risk factors for early infantile atopic dermatitis" Pediatr Allergy Immunol., 18(5):441-7 (2007).

Hughes, Timothy et al. "Functional discovery via a compendium of expression profiles" Cell vol. 102, 2000, pp. 109-126.

Bier et al., "DNA Microarrays" Adv. Biochem. Eng. Biotechnol., 109:433-53 (2008).

Hoheisel, "Microarray Technology: Beyond Transcript Profiling and Genotype Analysis" Nat. Rev. Genet., 7:200-10 (2006).

Fan et al., "Illumine universal bead arrays" Methods Enzymol., 410:57-73 (2006).

Raqoussis & Elvidger, "Affymetrix GeneChip system: moving from research to the Clinic" Expert Rev. Mol. Diagn., 6:145-52 (2006).

Mockler et al., "Applications of DNA tiling arrays for whole-genome analysis" Genomics, 85:1-15 (2005).

Lamb et al. "Gene Set Enrichment Analysis: A Knowledge Based Approach for Interpreting Genome-wide Expression profiles", Proc. Natl.Acad Sci U.S.A, 102, 15545-15550.

Trivedi, N. et al., "Gene array expression profiling in acne lesions reveals marked upregulation of genes involved in inflammation and matrix remodeling," J Invest Dermatol;126(5):1071-9 (2006).

Plager, D. et al. "Early cutaneous gene transcription changes in adult atopic dermatitis and potential clinical implications," Exp Dermatol;16(1):28-36 (2007).

Olsson, M. et al. "Increased expression of aquaporin 3 in atopic eczema," Allergy; 61(9):1132-7.

(56) References Cited

OTHER PUBLICATIONS

Mobini, R. et al. "A module-based analytical strategy to identify novel disease-associated genes shows an inhibitory role for interleukin 7 Receptor in allergic inflammation," BMC Syst Biol; 3:19 (2009).
Nair et al., "Genome-wide scan reveals association of psoriasis with IL-23 and NF-kappaB pathways," Nat Genet; 41(2):199-204(2009).
Swindell et al., "Genome-wide expression profiling of five mouse models identifies similarities and differences with human psoriasis," PLoS One; 6(4); Apr. 2011; 20 pages.
Lamb, Justin, et al. "Connectivity Map: Gene Expression Signatures to Connect Small Molecules, Genes, and Disease", Science, vol. 313, pp. 1929-1935; Sep. 29, 2006.

* cited by examiner

IL-1B (100pg/ml) daily
Fold Regulation vs control

|     | 24hr  | 48hr | 72hr | 96hr | 10day |
|-----|-------|------|------|------|-------|
| IL8 | 3.28  | 2.58 | 7.88 | 5.47 | 9.02  |
| IL6 | 1.52  | 1.73 | 3.58 | 1.55 | 5.94  |
| TNF | -1.21 | 1.34 | 1.37 | 2.67 | 1.19  |

$p \leq 0.05$
$p \leq 0.1$

| IL-17/IL-22 10ng/ml daily | | | | | | |
|---|---|---|---|---|---|---|
| | 24hr | 48hr | 72hr | 96hr | 6day | 10day |
| IL8 | 2.19 | 3.95 | 2.81 | 6.75 | 5.66 | 3.44 |
| TNF | -1.03 | 1.44 | 1.2 | 2.30 | -1.39 | -1.99 |
| IL6 | 1.87 | 2.92 | 1.98 | 3.00 | 3.05 | 3.61 |

| IL-17/IL-22 20ng/ml daily | | | | | | |
|---|---|---|---|---|---|---|
| | 24hr | 48hr | 72hr | 96hr | 6day | 10day |
| IL8 | 4.28 | 4.32 | 5.01 | 13.73 | 4.43 | 6.01 |
| TNF | -1.17 | 1.51 | 1.73 | 2.06 | -2.06 | -3.73 |
| IL6 | 2.56 | 2.53 | 2.94 | 3.94 | 3.38 | 4.86 |

$p \leq 0.05$
$p \leq 0.1$

|  | IL-17 200ng/ml + IL-22 20ng/ml | Clobetasol | IL-17 200ng/ml + IL-22 20ng/ml + Clobetasol 10uM |
|---|---|---|---|
| S100A7 | 37.97 | -1.11 | 22.55 |
| IL8 | 11.03 | -1.92 | 3.02 |
| IL6 | 3.96 | -3.37 | -3.66 |
| DEFB4 | 927.25 | 1.68 | 246.85 |
| KRT10 | -504.91 | -1.94 | -36.74 |
| KRT6A | 1.13 | -4.10 | -1.01 |
| TNF | -1.15 | 1.50 | -1.70 |
| FLG | -41.63 | 2.36 | -78.45 |
| CALML5 | -4.35 | 3.49 | -4.34 |

$p \leq 0.05$
$p < 0.1$

|  | tissue #1 | tissue #2 | tissue #3 | tissue #4 | tissue #5 |
|---|---|---|---|---|---|
|  | 10uM Clobetasol | | | | |
| IL8 | -2.72 | -2.72 | -3.68 | -3.89 | -1.76 |
| IL6 | -3.28 | -3.55 | -8.69 | -5.70 | -2.20 | p≤0.05
p<0.1

FIG. 10

| Tissue treated for 96hrs with 20ng/ml IL-17 + 20ng/ml IL-22 | | | | | |
|---|---|---|---|---|---|
|  | Tissue 1 | Tissue 2 | Tissue 3 | Tissue 4 | Tissue 5 |
| S100A7 | 4.11 | 11.56 | 4.86 | 1.64 | 3.86 |
| IL8 | 2.40 | 17.49 | 4.36 | 2.35 | 4.47 |
| IL6 | 2.11 | 2.53 | 3.06 | 2.15 | 4.85 |
| DEFB4 | 12.85 | 46.24 | 103.63 | 9.85 | 60.66 |
| KRT10 | -4.02 | -3.73 | -17.18 | -1.60 | -6.80 |
| KRT6A | 1.18 | 2.64 | 1.95 | 2.01 | 1.47 |
| TNF | 1.51 | 1.10 | 4.97 | 1.86 | 1.16 |
| FLG | -12.73 | -8.80 | -46.83 | -37.88 | -4.64 |
| CALML5 | 2.36 | -1.39 | 6.79 | -3.10 | 1.46 | p≤0.05
p<0.1

FIG. 11

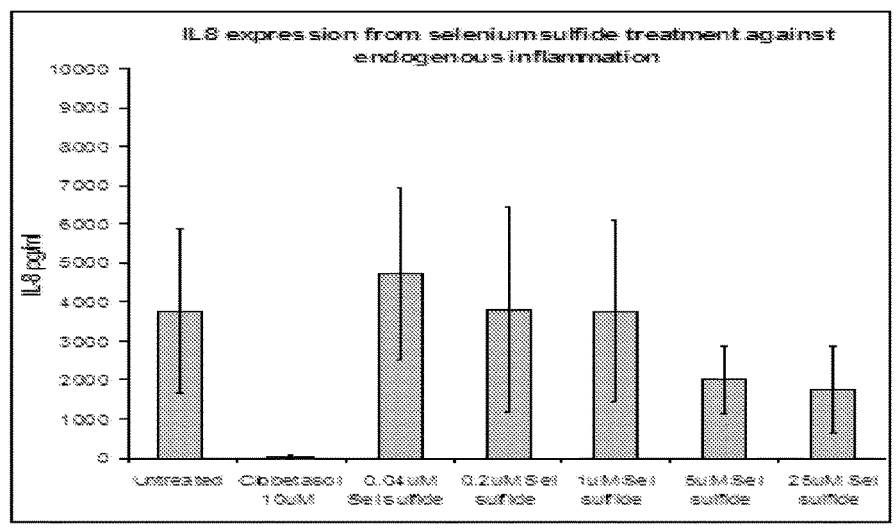
FIG. 12
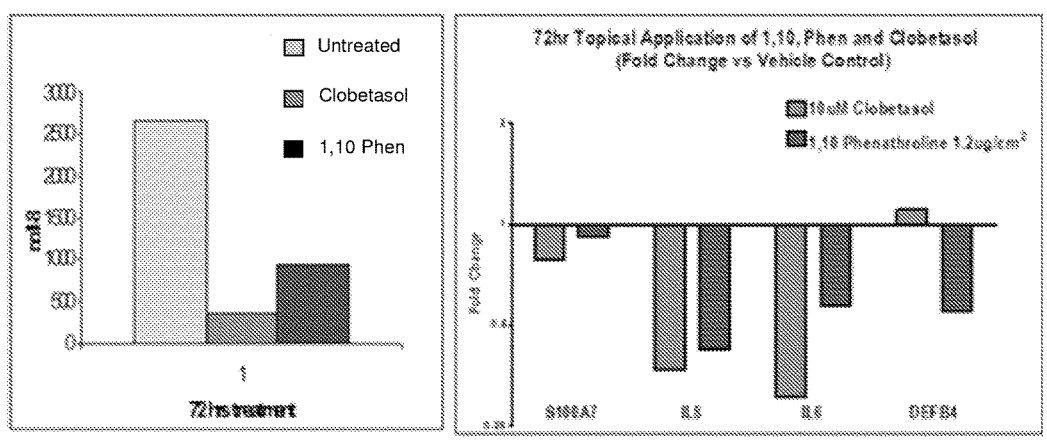
FIG. 13A
FIG. 13B

HUMAN EX VIVO SKIN MODEL AND ITS USE IN METHODS OF IDENTIFYING MODULATORS OF SKIN INFLAMMATION

TECHNICAL FIELD

The disclosure relates to a method of identifying modulators of inflammation of the skin comprising use of an ex vivo human skin model. The disclosure relates generally to the field of skin care.

BACKGROUND

Skin is a complex, multi-layered, large, and visible organ of the mammalian (e.g., human) body that is important to health and, for self-aware mammals such as humans, self-image. Skin comprises three principal layers (i.e., the epidermis, the dermis, and the hypodermis or subcutis) that contain a variety of cell types and structures, including epidermal and dermal connective tissue with blood and lymphatic vessels, hypodermal adipose tissue, and elastic fascia beneath the hypodermis. In turn, these structures are composed of a number of different cell types including keratinocytes, melanocytes, fibroblasts, endothelial cells, and adipocytes.

The skin functions, in part, as an immune organ, acting as a barrier against environmental factors and mounting an inflammatory response to such factors, when necessary, in order to protect against injury and infection. In this role, skin brings to bear several types of immune cells such as macrophages, dendritic cells, mast cells, and T-cells. These cells provide not only protective immunosurveillance against foreign objects such as microbes, they also release cellular factors to maintain homeostasis, including factors that regulate inflammation of the skin. Various factors involved in regulating skin inflammation (e.g., interleukins), promote homeostasis in response to a variety of health-related conditions, such as eczema, psoriasis, wounds, bacterial exposure, and dandruff. Moreover, the inflammatory response mounted by skin can arise in different ways. For example, the release of pro-inflammatory cytokines can induce inflammation in skin, as can a mechanical breach of skin integrity. Although skin inflammation can arise in a number of ways, however, these inflammatory responses do share common characteristics at both the molecular and physiological level.

Given the undesirable impact that skin-related inflammation can have on one's health, appearance and self-esteem, there is continuing interest in identifying cosmetic and/or therapeutic agents that are effective for treating or improving the appearance of skin by modulating skin inflammation. Skin models capable of more closely mimicking the in vivo skin condition would be expected to increase the accuracy of identifying modulators of skin inflammation.

Modeling techniques to study skin physiology and skin responses to agents have historically included a variety of specific techniques, from the culturing of a single cell type or a small number of commingled cell types, to fabricating tissue equivalents, to developing animal models. These relatively simple models, however, often lack entire skin layers, or particular skin cell types or structures, or intra- and/or inter-cellular communications found with skin in the in vivo condition. For example, cell cultures of single cell types are readily available but lack connections to other features of skin and often exhibit behavior in culture that is not seen in the in vivo skin condition. Additionally, such cells may be altered by genetic manipulation to promote cell passaging and maintenance.

More complex skin models include animal models and skin-equivalent models. While having additional complexity, animal models can suffer from limitations including genetic differences relative to human skin. Results obtained with animal models, moreover, are burdened with the concern that human skin tissues might react differently.

Skin-equivalent models can be limited by lack of cellular interconnectivity, permeability concerns, and anatomical simplicity. Some recent attempts at skin-equivalent models may be described as organotypic human tissue equivalents and include in vitro reconstructions of human cells such as keratinocytes cultured on an inert polycarbonate filter. These models, by their nature, are limited in that they can have reduced barrier function that can lead to aberrant sensitivities to tested agents. The models may also be less complex than human skin, having perhaps one or two cells types (such as keratinocytes and fibroblasts or keratinocytes and melanocytes), but lacking additional cells such as endothelial cells or even the full keratinocyte, fibroblast, and melanocyte combination. In addition, the organotypic skin-equivalent models may also be missing normal skin structures, such as glands, that may affect skin response.

The most complex skin model involves the ex vivo culture of human skin tissue samples. Some previous attempts at such models included small biopsies of skin floating directly in culturing media. It is known in the art that transient cultures may be deficient, as inventors and researchers have indicated attempts at ex vivo pig skin grafts are limited to seven days (Vielhaber et al., Ex vivo Human Skin Model, US2009/0298113). Attempts at improving the longevity of ex vivo skin have been sought, one example being described in EP 2 019 316 B1. Three-dimensional culture of skin cells has also been attempted, but those efforts focused on culturing immature fetal cells that had markedly different compositions from mature human skin in terms of the relative frequency of stem cells, the level of damaged cells, and the extent of senescent cells within the culture. Collectively, these differences establish the 3-D cultures as distinct from cultures of mature in vivo skin.

Even more recent ex vivo skin models have involved attempting to culture skin explants on metal grids (Mitts et al., Elastin Protective Polyphenolics and Methods of Using the Same, US2009/0110709) and skin grafting to the chorioallantoic membrane (CAM) of a fertilized ovarian egg (Goldstein et al., Chimeric Avian-Based Screening System Containing Mammalian Grafts, US2009/0064349). Such models, however, remain vulnerable to transient lifespans, excessive sensitivity to environmental influences (e.g., nutrient availability, toxin concentrations, heat), and the aforementioned limits on the ability to extrapolate results across species boundaries.

Beyond the difficulties in developing a skin model that accurately and precisely mimics the in vivo skin condition in efforts to identify agents such as modulators of skin inflammation, a method for identifying such modulators must identify controls that behave predictably with the skin model and in vivo skin. In addition, for screens relying on the larger inflammatory responses associated with induced inflammation, it is difficult to identify a level of inducer that will result in a significant inflammatory response without unacceptable additional effects such as the induction of proliferation. For example, IL-22 is an inflammation inducer that is also an inducer of cell proliferation. Depending on dosage and time, such inducers provoke a thickened hyperplastic response in skin samples, progressively destroying the integrity of the skin sample. Further, for screens designed to allow an inflammatory state to stabilize or normalize, inducer administrations (quantity and frequency) need to be compatible with extended culturing periods.

In view of the foregoing observations, it is apparent that human skin inflammation is associated with a variety of diseases and disorders, and there remains a need in the art for improved methods of identifying modulators of skin inflammation as well as the modulators themselves and methods of using such modulators to treat, prevent, or ameliorate a symptom associated with skin inflammation, or simply to improve the cosmetic appearance of skin. A need also exists for identifying conditions under which organ samples suitable for use in modeling inflammation, such as ex vivo skin samples can be maintained and/or grown in culture for extended times without significant deviation from the behavior of such materials in vivo.

SUMMARY

The disclosed subject matter satisfies at least one of the aforementioned needs in the art in providing an ex vivo human skin model that more accurately and reproducibly mirrors the in vivo skin environment. Use of the human skin model in methods of identifying modulators of skin inflammation provides the benefits of relying on a readily produced model that reduces errors in screening assays. By more accurately mirroring the in vivo environment of the skin, the model reduces screening misidentifications in the form of false positives and false negatives.

With the model and the disclosed methods of identifying modulators of endogenous and/or induced skin inflammation, the search for effective anti-inflammatories will increase in pace while decreasing in cost, leading to the realization of health, cosmetic and financial benefits.

One aspect of the disclosure provides a method of identifying a modulator of an inflammatory response comprising (a) contacting an ex vivo human skin sample comprising an epidermal layer and a dermal layer with a candidate modulator, wherein the ex vivo human skin sample is selected from the group consisting of an endogenously inflamed ex vivo human skin sample and an induced inflamed ex vivo human skin sample; (b) measuring the level of at least one marker of inflammation in the ex vivo human skin sample; and (c) identifying the candidate modulator as a modulator of an inflammatory response based on the level of the marker of inflammation in the ex vivo human skin sample relative to a control level of the marker of inflammation. The ex vivo human skin sample used in the methods may be an endogenously inflamed ex vivo human skin sample or an ex vivo human skin sample in which inflammation has been induced.

BRIEF DESCRIPTION OF THE DRAWINGS

FIG. 10 is an illustration of a response by ex vivo skin samples obtained from different donors to an inflammation modulator.

FIG. 11 is an illustration of a response by ex vivo skin samples obtained from different donors to an inflammation inducer.

FIG. 12 is an illustration of a response by the ex vivo skin model to inflammation modulators.

FIGS. 13A and 13B are illustrations of responses by the ex vivo skin model to inflammation modulators.

DETAILED DESCRIPTION

Figures 1, 2, 3:
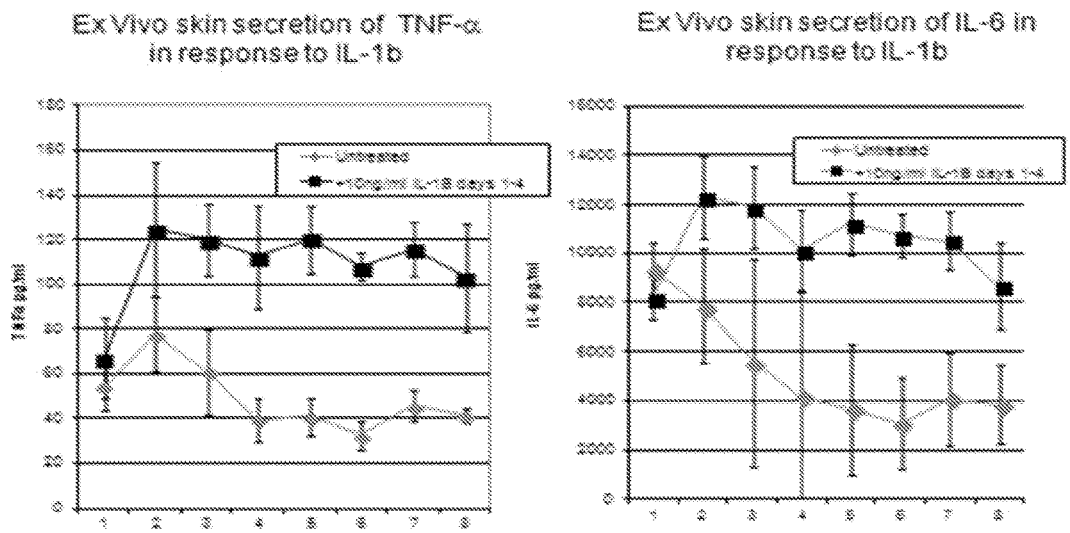
FIG. 1 is an illustration of a response by the ex vivo skin model to an inflammation inducer.
FIG. 2 is an illustration of a response by the ex vivo skin model to an inflammation inducer.
FIG. 3 is an illustration of a response by the ex vivo skin model to an inflammation inducer.

The materials and methods disclosed herein provide an efficient and economical approach to the identification and use of modulators of human skin inflammation, such as human skin inflammation, that find use in cosmetic and therapeutic applications to improve the appearance of skin in terms of color, texture, perceptible tension and other skin attributes, as well as to treat, prevent, or ameliorate a symptom of a human skin disease, disorder or condition. The methods for identifying modulators of skin inflammation use an ex vivo human skin model comprising the epidermal and dermal layers of human skin, resulting in methods that accommodate endogenous and/or induced inflammatory states while retaining regulatory control over the inflammation, leading to more accurate and precise identifications of modulators than previous in vitro and artificial or non-human skin-based approaches to the identification of modulators of skin inflammation. The disclosure identifies sets of conditions that allow for the maintenance and/or growth of the ex vivo skin model under conditions that resemble conditions in vivo, thereby permitting use of the model to efficiently and effectively identify modulator of skin inflammation with greater certainty, reliability and reproducibility than could be achieved by screens known in the art.

Other features and advantages of the present disclosure will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

The human ex vivo skin model herein comprises an epidermal layer (e.g., keratinocytes, melanocytes and langerhan cells) and a dermal layer (e.g., fibroblasts, vasulature and resident immune cells) and is capable of accurately reproducing regulated inflammatory responses observed in human skin in vivo. The capacity of the model to mimic the in vivo human skin context more accurately than alternative cell and tissue culture approaches, non-human skin models, or synthetic skin models, results in improved screening methods for modulators of skin inflammation. The improved screening methods herein provide a more complete picture of cell response than conventional screens, which typically use cell or tissue cultures or non-human or synthetic skin models. As a consequence, the effort to identify anti-inflammatory therapeutics, prophylactics and cosmetics useful in addressing a variety of diseases, disorders and conditions of the skin is reduced and made more cost-effective, e.g., by reducing the frequency of false positives that look promising in cell or tissue culture but lack efficacy in the in vivo environment. As described further herein, the disclosure provides an ex vivo human skin model, methods of screening for or identifying modulators of endogenous (i.e., basal) or induced skin inflammation, and the compounds and compositions identified thereby.

The disclosure provides screening methods, i.e., methods for identifying modulators of an inflammatory response in skin, the method comprising providing a cultured human ex vivo skin sample comprising an epidermal layer and dermal layer; contacting the human skin sample with at least one candidate modulator of an inflammatory response in skin; and measuring the level of at least one marker of inflammation. In some embodiments, a control is provided, allowing a comparison of the level of marker expression resulting from contact with a candidate modulator to the level of expression of that marker in a tissue contacted with a control compound known to have a certain effect on inflammation, such as inhibition of inflammation. A final step in these embodiments is identifying a candidate modulator as a modulator of an inflammatory response where a statistically significant difference ($p \leq 0.10$) is observed between the expression level of at least one marker in tissue either exposed to the candidate modulator or exposed to the control.

The disclosure also provides a method for identifying modulators of an inflammatory response in skin, the method comprising providing a first and second ex vivo skin samples; inducing inflammation in the skin samples by contacting the first and second skin samples with at least one inducer of inflammation; exposing the second skin sample to a control, e.g., an inhibitor of inflammation; contacting the first and second skin samples with at least one candidate modulator of an inflammatory response in skin; measuring the level of at least one marker of inflammation in the first and second skin samples; comparing the expression level of the marker of inflammation in the first skin sample to the expression level in the second skin sample; and identifying a candidate modulator as a modulator of an inflammatory response where the expression levels for at least one marker of inflammation differ in a statistically significant manner ($p \leq 0.10$) between the first and second ex vivo skin samples.

Methods of identifying modulators of skin inflammation using an ex vivo human skin model generally comprise contacting an ex vivo skin sample with a candidate modulator of skin inflammation and measuring the resultant level of an inflammation marker. In addition, the methods according to the disclosure may further comprise obtaining a skin sample (e.g., obtaining surgical waste donor tissue), preparing the sample (e.g., by removing the subcutis), preparing the sample for tissue or organ culturing, contacting the sample with at least one candidate modulator applied topically or within the culture medium, incubating (e.g., culturing) the sample for a period of time, and measuring the level of at least one inflammation marker (e.g., gene transcription level, protein level, active protein level). Following the next section expressly defining terms used throughout this disclosure are sections in which the features of the ex vivo skin model and methods of identifying modulators of skin inflammation are described in greater detail.

DEFINITIONS

"Candidate modulator" means any synthetic or naturally occurring chemical compound selected for its potential use as a modulator of inflammation. Candidate modulators can be purified or in a mixture. Candidate modulators include small molecules, macromolecules, and polymers. In certain embodiments, a candidate modulator may be a recombinantly produced molecule contained or produced in a combinatorial library. In certain embodiments, a candidate modulator may be a molecule and macromolecule whose structure is designed by computer or three-dimensional analysis. "Candidate modulator" also includes crude or purified extracts of organic sources (e.g., animal extracts, botanical extracts, and microbial lysates). Candidate modulators for use in practicing the methods herein may be combined with an inert buffer (e.g., saline) or a suitable solvent (e.g., dimethylsulfoxide (DMSO), alcohols such as methanol and ethanol, and aqueous solutions such as water and culture medium).

"Dermatologically acceptable carrier" means a carrier that is suitable for topical application to the keratinous tissue, has good aesthetic properties, is compatible with other components in the dermatological composition, and will not cause any undesirable safety or toxicity concerns. The dermatologically acceptable carrier may be in a wide variety of forms such as, for example, simple solutions (water-based or oil-based), solid forms (e.g., gels or sticks) and emulsions.

"Dermatological composition" means a composition suitable for topical application on human skin and/or other keratinous tissue such as hair and nails.

"Endogenous inflammation" is synonymous with basal inflammation and means an inflammatory state or inflammatory response that arises in an ex vivo human skin sample without any purposeful human intervention to induce or create an inflammatory state or inflammatory response. Without wishing to be bound by theory, it is believed that endogenous inflammation arises in ex vivo human skin samples as a result of preparing the samples, e.g., the physical or mechanical separation of skin from the host organism and/or the division of skin into skin samples. Inflammation marker expression in endogenously inflamed cells, tissue or organs is significantly less-pronounced than the expression level changes seen under induced inflammation conditions.

"Humidity" herein means relative humidity.

"Increase" means an increase above a basal level, or as compared to a control. Conversely, "decrease" means a decrease below a basal level, or as compared to a control.

"Inflammation" means the response in skin to stimulus perceived by the skin as foreign or abnormal. Inflammation in skin may be characterized by redness, pain, swelling and heat, as would be understood in the art. Inflammation further means a cell, tissue or organ exhibiting an expression pattern or profile characteristic of, or consistent with, an inflammatory state. For example, inflammation includes a cell, tissue or organ in which expression is elevated for inflammation markers that exhibit increased expression in an inflamed state, and/or in which expression is lowered for inflammation markers that exhibit decreased expression in an inflamed state. Some non-limiting examples of inflammation markers that exhibit increased expression in an inflamed cell, tissue or organ include IL-6, IL-1β, IL-1α, TNF-α, TNF-β, and IL-8.

"Induced inflammation" means an inflammatory state, or inflammatory response, of a cell, tissue or organ that has been induced by the addition of an inflammation inducer. Any inflammation inducer known in the art or disclosed herein may be delivered to a cell, tissue or organ, such as an ex vivo human skin sample, to induce inflammation. Exemplary inflammation inducers include IL-22, IL-17, the combination of IL-22 and IL-17, and IL-1β. The induced inflammatory response is significantly more robust in terms of inflammation marker expression level changes than the endogenous inflammatory response (see below).

An "inducer of inflammation" is a physical, chemical, or biochemical entity capable of inducing inflammation in the skin of at least one mammal under at least one set of conditions. Exemplary inducers of inflammation include mechanical disruption of skin (e.g., surgery, physical rending of skin as by punching out discrete samples from a skin source), pro-inflammatory cytokines such as IL-17, IL-22, and IL-1β, microbial infection, and any other pro-inflammatory molecule or entity (including a physical force) known in the art.

An "inflammation marker" or "marker of inflammation" is an expressible element, or the element expressed thereby, that exhibits a change in expression level in a cell, tissue or organ that is inflamed versus a cell, tissue or organ that is not inflamed. Some inflammation markers exhibit statistically significant ($p \leq 0.10$) differences in expression level in inflamed versus non-inflamed cells, tissues or organs. For example, a "marker of inflammation" may be a gene, gene fragment, or coding region expressed at a detectably different level in cells contained in inflamed tissue relative to cells of the same type contained in like tissue that is not inflamed. The expression may involve RNA production (e.g., mRNA) or protein production, as measured by the physical presence of protein or by some activity characteristic of the protein.

"Metabolism" means any chemical reaction occurring inside a microorganism. Metabolism includes anabolism, the synthesis of the biological molecules (e.g., protein synthesis and DNA replication) and catabolism, the breakdown of biological molecules.

"Skin" means the epidermis, dermis, and hypodermis (i.e., subcutis), and also includes the mucosa and skin adenexa, particularly hair follicles, hair roots, hair bulbs, the ventral epithelial layer of the nail bed (lectulus) as well as sebaceous glands and perspiratory glands (eccrine and apocrine).

"Skin care" means regulating and/or improving skin condition. Non-limiting examples of skin care include improving skin health, skin hydration and the function of skin as a barrier.

"Skin model" means a model of human skin that includes an epidermis and a dermis. A skin model may optionally include a hypodermis.

"Topical" means the surface of the skin or other keratinous tissue. Dermatological composition includes any cosmetic, nail, or skin care product.

"PCR" means polymerase chain reaction and includes real-time PCR, quantitative PCR ("qPCR"), semi-quantitative PCR, and any combination thereof.

The articles "a" and "an" are understood to mean one or more of what is being claimed and/or described.

I. EX VIVO SKIN MODEL

Donor Skin

Donor skin suitable for use herein may be obtained from any suitable source, such as surgical waste (e.g., human skin) and slaughterhouses (e.g., livestock, including pigs). In some embodiments, the ex vivo skin may be divided up into a number of samples by mechanical separation. Although not required, the relatively fatty subcutis layer of the skin may be removed by any means known in the art, such as by scraping or cutting, and this removal is usually accomplished before dividing the skin into discrete samples, which can be of any size, including sizes as small as a few millimeters in diameter. Removal of the subcutis layer can improve absorption of the media into the remaining skin tissues (i.e., epidermis and dermis) during culturing, thereby providing a skin model that is suitable for either topical or media delivery of candidate modulators of inflammation. With skin samples ranging from 0.5 $cm^2$ to $cm^2$, multiple samples can be obtained from the same source skin, which allows for comparative testing between different candidate modulators or between a candidate modulator and a control. Suitable controls include positive controls provided by known inhibitors of skin inflammation, described below, and negative controls, such as inert compounds (i.e., compounds known not to affect skin inflammation) or no compound at all being brought into contact with a skin sample.

Skin Sample Culturing

Investigations of eukaryotic biology, such as human biology, often rely on ex vivo biological material. Frequently, the ex vivo biological material is an immortalized cell type, which exhibits the property of continued growth in culture. Primary cell cultures can suffer from limited passages of the cells, in turn limiting the studies that can be undertaken. A drawback of using immortalized cell lines is that these cells may not accurately reflect in vivo behavior because most healthy eukaryotic cells in the in vivo environment do not exhibit extended growth and, often, cannot even be maintained for extended times.

To obtain the advantages of a system more closely reflecting the in vivo condition, the ex vivo skin samples disclosed herein were subjected to extensive studies of the variables affecting their growth and maintenance. In theory, human body temperature of 37° C. would bring the methods closest to the in vivo condition in terms of temperature, but at such a relatively high temperature, ex vivo cells, tissues and organs tend to lose viability more rapidly than at lower temperatures. In addition, as disclosed herein, the methods of identifying modulators of skin inflammation using the ex vivo human skin model often take 4-6 days, or more, of culturing to ensure that an inflammatory response has been sustained and regulated as it would be in an in vivo environment. Over such a period, ex vivo biological materials often lose viability and begin to degrade. For example, an inflammatory state induced by a known inflammatory modulator such as IL-22 also places the ex vivo skin model at risk of increased cell proliferation, confounding and impeding the ability to accurately assess effects on inflammation marker expression levels. Surprisingly, is has been discovered that controlling humidity impacts the temperature and time effects on the viability of ex vivo skin. In particular, is has been unexpectedly discovered that providing a relative humidity of skin model maintenance/culturing of about 50% permitted an elevation in temperature to 37° C. without unacceptable loss of viability over the course of 4-6 days, which in some instances may be required to demonstrate an effect on inflammation.

Ex vivo skin samples suitable for use in the present model may be cultured or maintained, in a suitable culture medium such as, for example, Dulbecco's Modified Eagle's Medium (DMEM), optionally supplemented with serum (e.g., 10% fetal calf serum), or any other suitable medium known in the art for culturing eukaryotic cells or tissues. The temperature of the skin samples may be selected to correspond to the in vivo temperature (e.g., 37° C.) but may be varied as desired. For example, when using lipid metabolism genes, gene fragments or coding regions as inflammation markers, assay duration may exceed 10 days. In this example, it may be desirable to maintain the temperature of the ex vivo skin samples at 37° C. for the first 4-6 days, and at 33° C. for the remainder of the assay period.

The ex vivo skin samples may be cultured in a suitable container (e.g., multi-well plate) with the dermis side down over an iso-osmotic solution to keep the dermis moist and the epidermis dry. Additionally or alternatively, the ex vivo skin can be placed in a non-osmotic (non-isotonic) solution (i.e., partially or totally submerged). A suitable example of an iso-osmotic (or isotonic) solution is Dulbecco's Modified Eagle Medium (DMEM), but any suitable equivalent may be used. The solutions may include anti-mycotic or antibacterial reagents. The ex vivo tissue culturing conditions (e.g., time, temperature and/or humidity), are factors that can affect the performance of the present ex vivo skin model and corresponding screening methods.

Humidity

Longevity of the ex vivo tissues can be improved by selecting a suitable humidity. Typical eukaryotic cell and tissue cultures are incubated in an environment of about 95% humidity. Through a number of studies of the conditions required to support ex vivo human skin samples, it was discovered that lowering the humidity of organ culture would allow for extended maintenance and/or growth of the skin samples at 37° C. without significant apparent deviation from in vivo behavior. As demonstrated in the Examples below, reducing the humidity to about 50% resulted in notable increases in the viability of ex vivo skin samples, particularly when such samples had been incubated for at least 10 days. By selecting a suitable humidity, it may be possible to culture ex vivo skin sample at even higher temperatures by reducing the humidity and still maintain viability and/or consistent gene regulation of the ex vivo skin model.

Time

The time of incubation for an ex vivo skin sample herein may vary from several hours to ten days or more. For large-scale screening efforts a short incubation time may be beneficial. The ex vivo skin sample should be incubated for a sufficient time to allow the biological material to adapt to culture conditions and be responsive to an inducer of an inflammatory response as well as being responsive to a modulator of an inflammatory response. The ex vivo skin sample is often incubated in media for at least several hours. It is desirable to have skin samples that survive beyond ten days, since the expression patterns of at least some marker genes may require samples that have been incubated for at least 4, or at least 7, or at least 10 days, or at least 19 days. Marker genes, of course, exhibit expression patterns that differ in cells of inflamed tissue versus cells of tissue that is not inflamed. Exemplary marker genes that either require several days to become indicative of inflammation or remain indicative of inflammation over that period include genes encoding gene products involved in lipid metabolism, such as ceramide synthase 3 and HMG Co-enzyme A Receptor (HMGCR).

Temperature

One difficulty in establishing an ex vivo skin model that behaves like in vivo skin, and would therefore provide a more efficient and cost-effective system for identifying modulators of skin inflammation, is temperature. The in vivo temperature of 37° C. could not simply be imposed on the model system because that relatively high temperature leads to more rapid loss of in vivo behavior than lower temperatures, with the skin samples more quickly exhibiting abnormal physiological responses. In conventional ex vivo skin models it is not uncommon to maintain a temperature of about 33° C. to allow for ex vivo skin sample growth and maintenance, but this temperature results in a physiological environment that differs from in vivo conditions. Thus, it would be desirable to maintain a temperature that is closer to in vivo conditions (e.g., 37° C.) for at least a portion or even all of the assay. To establish conditions more closely aligned with in vivo conditions, several environmental properties may be varied. Surprisingly, a lowering of humidity to approximately 50% helps extend growth and maintenance of ex vivo skin cultures at 37° C. Although it may be desirable for most ex vivo human skin samples to be cultured and/or maintained at 37° C., it is contemplated that the incubation temperature for such skin samples can vary from 37° C. (e.g., from 37° C. to 33° C.) depending on the particulars of the method for identifying modulators of skin inflammation being used.

II. METHODS OF IDENTIFYING MODULATORS OF INFLAMMATION

The methods of identifying modulators of inflammation disclosed herein include methods incorporated into a tiered screening strategy for identifying a candidate modulator as a modulator of an inflammatory response in skin. For example, a first-tier screen could involve in silico efforts to identify candidate anti-inflammatory compounds, followed by an in vitro cell-based assay as a second tier. The method of identifying a modulator of skin inflammation comprising use of the present ex vivo human skin model may then be integrated into the multi-tiered approach as a third tier for identifying modulators.

Some embodiments of these identification methods may include providing a cultured skin sample, wherein the skin sample comprises an epidermal layer and a dermal layer; contacting the skin sample with at least one candidate modulator; generating a transcriptional profile from the skin sample, wherein the transcriptional profile comprises transcription levels of at least two marker genes selected from the group consisting of S100A7, IL8, IL6, DEFB4, KRT10, KRT6A, TNF (TNF-α), FLG, CALML5, ceramide synthase 3, and HMGCR; identifying a candidate modulator as a modulator of an inflammatory response in skin when the expression level of at least one of the marker genes differs from its expression level in a control transcriptional profile. In some embodiments, the skin sample is from a human.

The methods herein are scalable and, hence, are suitable for use in a variety of assay formats, including high throughput assay formats. The present methods can be performed with any number of candidate modulators, using ex vivo skin samples (e.g., human skin samples) of various sizes down to a few millimeters in diameter. Using relatively small ex vivo skin samples is compatible with the use of multi-well plates in screening methods designed to explore large numbers of candidate modulators, such as would be found in chemical, e.g., small molecule, libraries. Accordingly, the screening methods herein may be used for identifying an agent as a modulator of an inflammatory skin response, the method comprising (a) providing a cultured first skin sample, wherein the first skin sample comprises an epidermal layer and a dermal layer; (b) contacting the first skin sample with at least one candidate modulator; (c) generating a transcriptional profile from the first skin sample, wherein the transcriptional profile comprises transcription levels of at least two marker genes selected from the group consisting of S100A7, IL8, IL6, DEFB4, KRT10, KRT6A, TNF (TNF-α), FLG, CALML5, ceramide synthase 3, and HMGCR; (d) identifying the at least one candidate modulator as a modulator of an inflammatory response in skin when at least two genes selected from the group consisting of S100A7, IL8, IL6, DEFB4, KRT10, KRT6A, TNF (TNF-α), FLG, CALML5, ceramide synthase 3, and HMGCR differ in expression level from the same gene in an untreated control skin sample; and (e) repeating steps (a) to (d) to identify at least one modulator of an inflammatory response in skin, wherein the first skin sample and the candidate modulator are different for each repetition.

A candidate modulator may be identified as a modulator of an inflammatory response if it results in a detectable change in the expression level of at least one inflammation marker. In exemplary embodiments of the methods disclosed herein, the candidate modulator identified as a modulator will lead to a detectable down-regulation, i.e., decrease in expression level, of an inflammation marker such as IL-8 or IL-6. Methods that monitor the expression of more than one inflammation marker may increase the confidence in any resulting identifications of candidate modulators as modulators of skin inflammation. Additionally, confidence in identifications of candidate modulators as modulators of skin inflammation may be increased by confirming that a skin sample used to identify a modulator of skin inflammation, or another skin sample from the same source, is properly regulable, for example, by using a known inhibitor of inflammation, such as clobetasol, to ensure it provides the expected inhibitory effect on the expression of one or more inflammation markers.

The present disclosure provides a screening method for identifying a candidate modulator as an inhibitor of an inflammatory response in skin (e.g., human skin), the method comprising: (a) providing a cultured first skin sample, wherein the first skin sample comprises an epidermal layer and a dermal layer; (b) contacting the first skin sample with at least one candidate modulator; (c) generating a transcriptional profile for the first skin sample, wherein the transcriptional profile comprises transcription levels of at least two marker genes selected from the group consisting of S100A7, IL8, IL6, DEFB4, KRT10, KRT6A, TNF (TNF-α), FLG, CALML5, ceramide synthase 3, and HMGCR; (d) contacting a second skin sample with a positive control agent that induces a change (e.g., an increase or decrease) in transcription levels of the at least two marker genes selected from the group consisting of S100A7, IL8, IL6, DEFB4, KRT10, KRT6A, TNF (TNF-α), FLG, CALML5, ceramide synthase 3, and HMGCR, wherein the change is consistent with inhibition of an inflammatory response in skin; (e) generating a positive control transcriptional profile for the second skin sample; (f) identifying the at least one candidate modulator as effective for inhibiting an inflammatory response in skin when the transcriptional profile generated in (c) is directionally similar to the positive control transcriptional profile generated in (e).

III. CANDIDATE MODULATORS OF INFLAMMATION

Candidate modulators of inflammation can be any biochemical or chemical compound, including small molecules, biomolecules, and chemical polymers. The candidate modulators may be organized in compound libraries of any size, and may be synthetic in origin or derived from natural sources as compounds or more complex structures. In addition, candidate modulators may be compounds arising from rational design efforts, such as rational drug design programs, regardless of whether such efforts are computer-based or not. No limitations other than those expressly placed upon the structure or function of a candidate modulator herein are contemplated. Thus, any compound or material, including physical materials as well as chemical and/or biochemical molecules and more complex structures that can be used in the methods for identifying skin modulators is contemplated as a candidate modulator.

IV. CONTROLS—KNOWN INHIBITORS OF INFLAMMATION

To maximize the efficiency and cost savings of the methods of identifying modulators of skin inflammation disclosed herein, the ex vivo skin samples should exhibit behavior that tracks the behavior of in vivo skin as closely as possible. An important property of skin inflammation in mammals for purposes of the present method is that the inflammatory response is regulatable (regulable). A variety of known inhibitors of inflammation may be used to inhibit inflammation in the methods herein. Some nonlimiting examples of known inflammation inhibitors include clobetasol, 1,10-phenanthroline, apigenin, betamethasone, hydrocortisone, ketoprofen, arlatone, zinc pyrithione (ZPT), and selenium sulfide. At least some known inflammation inhibitors can inhibit both endogenous and induced inflammation (e.g., clobetasol), while some exhibit selectivity in inhibiting endogenous inflammation (e.g., apigenin) or induced inflammation (e.g., ZPT) more effectively than the other type of inflammation in ex vivo skin samples. In some embodiments, other compounds may be used to inhibit inflammation, such as BV-OSC, which is a stabilized form of vitamin C in the form of ascorbyl tetraisopalmitate ester (INCI name: tetrahexyldecyl ascorbate).

IV. INDUCERS OF INFLAMMATION

Any known inhibitor of inflammation may be suitable for use in the methods herein for identifying modulators of inflammation in ex vivo skin samples. Several known inflammation inducers are pro-inflammatory cytokines, and all such molecules are included within the scope of the disclosed methods. Particular examples of such cytokines are interleukin 17 (IL-17), interleukin 22 (/IL-22), and interleukin 1 beta (IL-1β or IL-1 beta). Also expressly contemplated are combinations of known inhibitors such as pro-inflammatory cytokines, including a combination of IL-17 and IL-22.

V. MARKERS OF INFLAMMATION

The human ex vivo skin model disclosed herein more accurately reflects the in vivo behavior and physiology of human skin as well as methods for identifying modulators of skin inflammation that use the present ex vivo skin model. The present methods of identifying modulators of skin inflammation contemplate the use of any known inflammation marker gene or encoded protein. Some suitable inflammation marker genes include, but are not limited to, genes encoding (and the encoded products) secreted cytokines, anti-bacterial proteins, lipid biosynthesis proteins, and gene/protein types represented by expressly disclosed inflammation markers herein. Exemplary inflammation markers include the following categories of marker genes known to be associated with inflammation in that expression levels vary between the inflamed and non-inflamed states. Interleukins such as, but not limited to, IL1A, IL1B, IL5, IL7, IL8, IL9, IL10, IL12, IL17A, IL17C, IL17F, IL19, IL21, IL23, IL27, IL31, and IL33 are contemplated, as are interleukin receptors including, but not limited to, IL10RA, IL10RB, IL1R1, IL5RA (CD125), and IL9R. Also comprehended by the disclosure are chemokines including, but not limited to, C5, Eotaxin, MCP-4, TARC, MCP-1, MIP-3A, CCL22, CCL23, MIP-1B, RANTES, MCP-3, MCP-2, CX3CL1, IL8RA, INP10, L8RB, and CXCL3, as well as chemokine receptors including, but not limited to, CCL13 (MCP-4), CCR1, CCR2, CCR3, CCR4, CCR5, CCR6, CCR8, CX3CR1, CXCR1, and CXCR2. Additionally contemplated are other Cytokines such as, but not limited to, MCP-1, GM-CSF, TNFSF5, MCSF, GCSF, TNFSF6, IFNA2, IFNG, TNFB, MIF, NAMPT, TNF, TRAIL, IFNA1, IFNG, and TNF, as well as other genes involved in inflammation including, but not limited to, CD4, CD40, TNFSF5, FASLG, JAK2, JNK1, NFκB1, RAG1, STAT1, the s100 family, and beta defensin.

In some embodiments, the method of identifying modulators of skin inflammation will measure the expression level(s) of at least one marker selected from the group consisting of S100A7, IL8, IL6, DEFB4, KRT10, KRT6A, TNF (TNF-α), FLG, CALML5, ceramide synthase 3, and HMGCR. In addition to exhibiting altered expression in the inflammatory state, these markers are recognized in the art for providing information useful in assessing the condition of the ex vivo skin model. For example, the keratin genes (KRT10 and KRT6A) as well as the FLG (Filaggrin) gene are known to provide a measure of cell proliferation in addition to varying expression between inflamed and non-inflamed states. β-defensin and S100A7 (Psoriasin) express anti-microbial peptides useful in combating infection. The expression of β-defensin and S100A7 demonstrate a tissue protective response to inflammation. IL-8 is commonly recognized as a chemokine serving as a major mediator of the inflammatory response by inducing chemotaxis of white blood cells involved in the immune response. IL-6 is secreted by T cells and macrophages to stimulate the immune response that contributes to inflammation. TNF is known to be an acute-phase protein involved in the acute-phase response that involves proteins whose levels vary during an inflammatory response. Calmodulin-like gene 5 ("CALML5") is expressed in skin and may help mediate inflammation. The expression of CALML5 is known to be regulated by certain inflammatory cytokines such as IL-22. Ceramide synthase 3 is believed to be required to avoid disruption of skin barrier function, which could lead to infection and inflammation. HMGCR, a target for some statins that are known to have anti-inflammatory properties, catalyzes a rate-limiting step in the synthesis of isoprenoids, which are part of the biochemical process for producing an inflammatory response.

In greater detail, the present disclosure provides screening methods for identifying a candidate modulator as a modulator of an inflammatory response in skin, the method comprising providing a cultured human skin tissue sample, wherein the skin sample comprises an epidermal layer and a dermal layer; contacting the skin sample with at least one candidate modulator; generating a test transcriptional profile from the skin sample, wherein the test transcriptional profile comprises transcription levels of at least two marker genes selected from the group consisting of S100A7, IL8, IL6, DEFB4, KRT10, KRT6A, TNF (TNF-α), FLG, CALML5, ceramide synthase 3, and HMGCR; and identifying the at least one candidate modulator as a modulator of an inflammatory response in skin when the test transcriptional profile differs from the control transcriptional profile with respect to the level of at least one of the marker genes.

The methods and models described herein can involve analysis of RNA or protein from full or partial human skin tissue samples or from simple cell types removed from such samples. Dermal and epidermal layers may be removed and analyzed separately or together. Protein levels either secreted into the media or extracted from whole tissue may be analyzed via standard protein analysis techniques (e.g., Western blot and ELISA). Transcriptional profiles can be generated from such individual cells, layers, or from multiple cells, layers, parts (or in whole) of the human skin tissue sample or samples. Gene expression measurements may be made using any suitable profiling technology. For example, the mRNA expression of the genes of interest may be determined using microarray techniques. Other emerging technologies that may be used include RNA-Seq or whole transcriptome sequencing using NextGen sequencing techniques. As used herein, the term "microarray" refers broadly to any ordered array of nucleic acids, oligonucleotides, proteins, small molecules, large molecules, and/or combinations thereof on a substrate that enables gene expression profiling of a biological sample. Microarrays are available from Affymetrix, Inc., Agilent Technologies, Inc., Illumina, Inc., GE Healthcare, Inc., Applied Biosystems, Inc., Beckman Coulter, Inc., and other manufacturers.

In various non-limiting examples, identifying compounds as effective modulators of skin inflammation can involve analyzing a panel of genes to identify inflammation marker genes and to assess whether expression of identified inflammation marker genes varies at the transcriptional level in response to candidate modulators. It is recognized that assessments of transcription may be improved by comparison to untreated controls (e.g., organ, tissue or cell samples not treated experimentally. Control material from the same source as the experimental material may also add to the strength of any such assessments. A determination that a candidate modulator is effective can also involve statistical tests and/or statistical significance of replicate wells or tests. For example, replicates could involve a sample size (n) of 3, 5, or 10 or more. Additionally, statistical significance of mRNA levels can be set at less than or equal to 0.1, 0.05, 0.01, 0.001, or can be set at alternate levels. A non-limiting example of mRNA extraction and PCR analysis is provided in Example 3.

VI. TYPES OF INFLAMMATION

The methods herein may utilize endogenous inflammation of ex vivo human skin samples and/or induced inflammation of ex vivo human skin samples to identify modulators of inflammation. Endogenous inflammation arises in skin samples physically removed from the organism and/or separated into individual samples, which may be analogized to skin wounding, a known cause of inflammation. At the molecular level, endogenous inflammation is relatively uncharacterized. In contrast, induced inflammation can be viewed as a more specific form of inflammation that is characterized at the molecular level to a greater extent than endogenous inflammation because it involves the molecular pathways associated with the inducer of inflammation being used. Although ex vivo skin samples exposed to an inducer of inflammation may also exhibit endogenous inflammation, the much greater magnitude of the induced inflammatory response allows one to measure or monitor the induced inflammatory response of ex vivo skin samples.

Some embodiments provide for an ex vivo model of a skin condition characterized by acute inflammation, the model comprising a cultured skin sample (e.g., human skin) in a culture medium, the skin sample having an epidermal and a dermal layer, and having been cultured in the culture medium at about 30° C. to about 40° C. at a relative humidity from about 50% to about 90% for a period of time from about 4 days to about 10 days, wherein acute inflammation of the skin sample is effectuated by contacting the skin sample with IL-1β.

Specific embodiments provide for an ex vivo model of a condition of skin characterized by chronic inflammation, the model comprising a cultured human skin sample in a culture medium, the human skin sample having an epidermal and a dermal layer, and having been cultured in the culture medium from between about 30° C. to about 40° C. at a relative humidity from about 50% to about 90% for a period of time from about 4 days to about 10 days, wherein chronic inflammation of the skin sample is effectuated by dosing the skin sample with IL-17 and IL-22.

VII. SCREENING METHODS

As previously discussed, human donor tissue samples can be derived from surgical waste tissue, be cultured on a membrane, or either include a subcutaneous fat layer or include a sample that has had the subcutaneous fat layer removed. In those embodiments where a human donor tissue sample is divided into at least a first and second human donor tissue sample, the subcutaneous fat layer can be removed before the dividing. Some of the tissue-divided samples may be dosed with a positive control, some of the divided tissue samples may be dosed with one or more candidate modulators, and some of the divided tissue samples may be used as untreated comparative controls (meaning not treated with either the positive control or a candidate modulator of interest).

The method according to the disclosure is amenable to repetitive use, i.e., the method may be performed multiple times in parallel (i.e., at the same time, as in high throughput formats) or in series (i.e., over time) to assess many candidates, such as would be found in a chemical library, or to confirm results with a particular candidate modulator. The method of identifying modulators of inflammation can be performed multiple times with skin samples from the same, or different, donors, e.g., human donors. Each repetition may also involve a different candidate modulator. A plurality of candidate modulators may be screened. In some embodiments, greater than about 5, 10, 25, 50, 100, 200, 400, 800 and/or less than about 1000, 2500, 5000, 10000, 20000, or 50000 candidate modulators may be screened. In some embodiments, the effect of 2, 4, 6, 10, 25, 50, 100, 200, 500 or more of the candidate modulators screened using ex vivo tissue from different donors may be compared to each other to identify which candidate modulators provide, relative to each other or the positive controls, the best regulation of the genes of interest to provide a desired cosmetic or therapeutic anti-inflammatory effect.

In some embodiments, the ex vivo skin tissue is contacted with at least one candidate modulator of interest or a positive control. The candidate modulator or positive control may be applied topically or via a suitable growth media. For topical applications, the ex vivo skin tissue may be dried (e.g., to remove any liquid media from the sample) prior to daily application of the material. The ex vivo skin tissue may be fed based on cellular metabolic rates. Feedings can be multiple times a day, every day, every other day, or on specific days throughout a multi-week period (such as 2, 3, or more). The feedings can vary depending on the temperature of the culture, such as daily feedings for cultures maintained at 37° C. and every other day for cultures maintained at 33° C.

The methods of identifying candidate modulators disclosed herein may also be combined with other screening methods to provide a tiered screening process. Tiers are associated with increased complexity per level. Because each tier provides additional data, conclusions can be drawn to more accurately focus on promising candidate modulators. Therefore, higher tiers are associated with lower numbers of candidate modulators that have higher probabilities of being effective. Tiers may, in some embodiments, advance as follows: enzyme assays, cell-based cultures, in vitro assays, ex vivo skin assays according to the disclosure and, optionally, in vivo skin assays. Initial tiers can be completed more quickly with higher outputs, while advanced tiers involve additional time and involve lower throughput. An in-depth analysis of each tier provides end data allowing increased probabilities of success for the candidate modulators.

VIII. COSMETIC COMPOSITIONS

Because of the desirability of providing various cosmetic compositions to combat skin inflammation, candidate modulators of skin inflammation identified by one or more of the methods and models described herein are formulated into cosmetic compositions suitable for topical application to the skin. In certain embodiments, the cosmetic composition may include a dermatologically acceptable carrier, the candidate modulator, and one or more optional ingredients of the kind commonly included in the particular cosmetic compositing being provided.

Dermatologically acceptable carriers should be safe for use in contact with human skin tissue. Suitable carriers may include water and/or water-miscible solvents. The cosmetic skin care composition may comprise from about 1% to about 95% by weight of water and/or water miscible solvent. The composition may comprise from about 1%, 3%, 5%, 10%, 15%, 20%, 25%, 30%, 35%, 40%, 45%, 50%, 55%, 60%, 65%, 70%, 75%, 80%, or 85% to about 90%, 85%, 80%, 75%, 70%, 65%, 60%, 55%, 50%, 45%, 40%, 35%, 30%, 25%, 20%, 15%, 10%, or 5% water and/or water miscible solvents. Suitable water miscible-solvents include monohydric alcohols, dihydric alcohols, polyhydric alcohols, glycerol, glycols, polyalkylene glycols such as polyethylene glycol, and mixtures thereof. Other suitable solvents include lower aliphatic alcohols such as ethanol, propanol, butanol, isopropanol; diols such as 1,2-propanediol,1,3-propanediol, butanediol, pentanediol, hexanediol, heptanediol, decanediol; glycerin; water, and mixtures thereof. In certain embodiments, the personal care composition comprises water, diols, glycerin, or combinations thereof. When the skin care composition is in the form of an emulsion, water and/or water-miscible solvents are carriers typically associated with the aqueous phase.

Suitable carriers also include oils. The skin care composition may comprise from about 1% to about 95% by weight of one or more oils. The composition may comprise from about 0.1%, 0.5%, 1%, 2%, 5%, 10%, 15%, 20%, 25%, 30%, 35%, 40%, 45%, 50%, 55%, 60%, 65%, 70%, 75%, 80%, 85%, or 90% to about 90%, 85%, 80%, 75%, 70%, 65%, 60%, 55%, 50%, 45%, 40%, 35%, 30%, 25%, 20%, 15%, 10%, 5%, or 3% of one or more oils. Oils may be used to solubilize, disperse, or carry materials that are not suitable for water or water-miscible solvents. Suitable oils include silicones, hydrocarbons, esters, amides, ethers, and mixtures thereof. Oils may be fluid at room temperature. The oils may be volatile or nonvolatile. "Non-volatile" means a material that exhibit a vapor pressure of no more than about 0.2 mm Hg at 25° C. at one atmosphere and/or a material that has a boiling point at one atmosphere of at least about 300° C. "Volatile" means that the material exhibits a vapor pressure of at least about 0.2 mm. of mercury at 20° C. Volatile oils may be used to provide a lighter feel when a heavy, greasy film is undesirable. When the skin care composition is in the form of an emulsion, oils are carriers typically associated with the oil phase.

The skin care composition may comprise an emulsifier. An emulsifier is particularly suitable when the composition is in the form of an emulsion or if immiscible materials are being combined. The skin care composition may comprise from about 0.05%, 0.1%, 0.2%, 0.3%, 0.5%, or 1% to about 20%, 10%, 5%, 3%, 2%, or 1% emulsifier. Emulsifiers may be nonionic, anionic or cationic. Examples of emulsifiers are known in the art and some are disclosed in U.S. Pat. No. 3,755,560, U.S. Pat. No. 4,421,769, and McCutcheon's, *Emulsifiers and Detergents*, 2010 Annual Ed., published by M. C. Publishing Co. Other suitable emulsifiers are further described in the Personal Care Product Council's *International Cosmetic Ingredient Dictionary and Handbook*, Thirteenth Edition, 2006, under the functional category of "Surfactants—Emulsifying Agents." The identifications of emulsifiers in each of these references are hereby incorporated by reference. Linear or branched type silicone emulsifiers may also be used. Particularly useful polyether modified silicones include KF-6011, KF-6012, KF-6013, KF-6015, KF-6015, KF-6017, KF-6043, KF-6028, and KF-6038 from Shin Etsu. Also particularly useful are the polyglycerolated linear or branched siloxane emulsifiers including KF-6100, KF-6104, and KF-6105 from Shin Etsu. Emulsifiers also include emulsifying silicone elastomers.

The skin care compositions may be generally prepared by methods known in the art of making cosmetic compositions (or therapeutic compositions) and, in particular, topical compositions. Such methods may involve mixing of ingredients in one or more steps to a relatively uniform state, with or without heating, cooling, application of vacuum, and the like. Emulsions may be prepared by first mixing the polar, aqueous-phase materials separately from the non-polar-phase materials and then combining the two phases as appropriate to yield the desired continuous phase. The composition may be provided in a package sized to store a sufficient amount of the composition for a treatment period. The size, shape, and design of the package may vary. Certain package examples are described in U.S. Pat. Nos. D570,707; D391,162; D516,436; D535,191; D542,660; D547,193; D547,661; D558,591; D563,221; 2009/0017080; 2007/0205226; and 2007/0040306, incorporated herein by reference.

IX. EXAMPLES

The following are non-limiting examples of various aspects of the methods and models described herein. The examples are given solely for the purpose of illustration and are not to be construed as limiting the invention, as many variations thereof are possible.

Example 1

Ex Vivo Skin Sample Preparation

This Example describes the materials and methods used in preparing ex vivo skin samples for use according to the methods disclosed herein. Materials used in preparation of ex vivo skin samples for use in the disclosed screening methods included: Dulbecco's Modified Eagle Medium (DMEM) plus Glutamax, antibiotic and antimycotics, 1× phosphate-buffered saline (PBS), 150×15 mm sterile culture dishes, sterile gauze 4×4, disposable safety scalpels, 4 mm disposable biopsy punch, 6-well cell-culture inserts, disinfected tweezers, cotton-tipped applicators, 6-well culture plates, ruled, disinfected cutting mat (12×12), scraper handle, tissue freezing medium, biopsy cassettes, frozen-tissue freezing vessels, 10% formalin, shipping containers for fixed tissue, and biohazard/sharps containers. Media was prepared in advance of the arrival of ex vivo skin. The skin arrived with the dermis (fat) side down on sterile DMEM soaked gauze in a sterile culture dish. The culture dish was taped shut and in a biohazard zip-lock baggie on an ice pack in a secondary container.

On arrival, the skin was removed from the bag and soaked in 3×DMEM media (3× refers to concentration of antibiotic and antimycotics) and stored at 4° C. for 1 hour. After 1 hour, the skin was removed from the 3×DMEM and rinsed with sterile 1×PBS. The skin was placed in a clean culture dish containing gauze soaked with 1×DMEM. The sample was put in culture the same day as arrival. If necessary, however, the ex vivo skin samples can be stored at 4° C. overnight.

In preparation for culture, the following was performed: on a cutting mat, the skin was flipped over so that the epidermis was down and the subcutis (fat) was exposed. The fat was removed with a disposable scalpel by carefully grasping one corner of the skin with sterile serrated forceps and scraping the fat away with the blade held at a 45° angle to the skin. After the fat was removed, the surgical edges were cut off with a scalpel using a scraper as a straight edge guide and to hold the skin in place. Using the scraper as a guide, the skin was cut into 1.25 cm (2×2 squares on grid) wide strips using a ruler to measure the width. The strip was rinsed in a 100 mm culture dish containing 1×PBS. The strips were cut into 1.25 cm$^2$ squares and placed in a 100 mm culture dish on 1×DMEM-soaked gauze until they were put into culture 30 minutes later.

Example 2

Culturing Ex Vivo Skin Samples

Culture plates were prepared that included 2.5 ml of media or media with treatment (e.g., a candidate modulator, an inflammation inducer, and/or an inhibitor of inflammation) in each well of a 6-well plate. One Millicell culture insert was added to each well and 100 μl of 1× DMEM was put in the center of each insert membrane. Squares of skin tissue were selected randomly and placed into each of the inserts (one piece of skin per insert), on top of the media on the membrane. The plates were stored at 33° C., with fresh media changes daily. As a control, baseline tissue measurements were collected from excess waste (cryogenics were used for snap-freezing). Baseline biopsy collection included two 4 mm punches for an MTT colorimetric assay (described below); one 4 mm punch was snap-frozen in OCT tissue compound for fresh histology; one 4 mm punch was fixed in 10% formalin and sent out for paraffin embedding. Expression measurements of inflammation marker genes were performed using PCR and primers appropriate to the known sequence of the gene(s) of interest.

Culturing and treatment of the ex vivo skin model comprised replicates of n=5. Before experimental treatment, compounds (e.g., a candidate modulator, an inflammation inducer, or a suppressor of inflammation) were solubilized in appropriate solvents (including PBS, media, alcohol, and DMSO). Appropriate dilutions were made for treatment and 15 ml of media was used per plate per day for treatment, with 2.5 ml of media per well under the cell culture insert. Media was pre-warmed and changed every day during the experiment. The media was aspirated and replaced with fresh, warmed media at a level of 2.5 ml per well. In some embodiments, some or all of the media may be collected prior to changing and analyzed for secreted protein.

Viability of the ex vivo skin cultures was assessed throughout the experiments and samples of tissue were collected for mRNA analysis. An MTT (3-(4,5-Dimethylthiazol-2-yl)-2,5-diphenyltetrazolium bromide) colorimetric assay was utilized to assess cellular viability. Cryogenics were used for sample collection.

The MTT plate was pre-labeled and 600 µl of 1 mg/ml MTT in DMEM was added to each well. All samples were 4 mm biopsies. Samples may be obtained using a biopsy punch (e.g., a Sklar 4 mm biopsy punch) and a hammer on a craft cutting mat (previously cleaned with alcohol), which allows distributing approximately equivalent sized samples from one treated piece of tissue across several analyses. In this example, 2 punches for RNA and 1 punch for MTT were generally taken. Additional punches may be taken for other measures such as protein endpoints as well. The hammer was lightly tapped to take the biopsy, working with one treatment group on a mat at a time to take all necessary punches. Two punches were placed in a screw cap tube and snap-frozen in liquid nitrogen. One punch per well was placed in an MTT plate. Time per treatment group to collect all samples was 5 minutes. Once all groups were processed, the MTT plate was placed in an incubator for 24 hours. Well plates (2 ml deep) were provided with 1 ml of isopropanol per sample. One sample was placed per well, and the well was sealed and labeled. The plates were placed at 4° C. for 3 days of extraction.

The MTT plate was read in the following manner: a 96-well clear, flat-bottom plate was used (though any cell culture plate can be used). Isopropanol was mixed in the deep well plate, after which 150 µl of each sample was transferred into the new 96-well plate. An EPOCH plate reader with GEN5 software was used, and an absorbance endpoint was chosen for use (e.g., 562 nm). The plate was placed in the reader and a reading was taken. Data was exported to an Excel sheet for manipulation and use.

Example 3

Methods and Materials Used to Assess Ex Vivo Skin

ELISA Measurement of Secreated Cytokines.

This method can be used to measure the presence of Cytokines using Meso Scale Discovery's ("MSD") standard ELISA bead assay protocol and MSD's cytokine specific reagents. The culture media is collected daily prior to feeding the tissue and stored frozen at approximately −80° C. until assayed. Prior to assay, standards are prepared and a dilution course is run to establish an appropriate dilution for analysis. Samples are incubated with anti-cytokine beads for 3 hours and run using a Bio-Rad Bioplex 100 instrument.

mRNA Processing and Purity Assessment

For cryopreparation and extraction of mRNA, the following equipment was obtained and prepared: 2 ml round bottom tubes were prepared with 1 ml of TRIZOL and a 5 mm stainless steel bead for each sample; a dry ice bucket was obtained and liquid nitrogen was placed in the bucket. Biopsy punches were maintained on dry ice, and samples remained frozen. Cryobags and covaris cryoprep were used in freeze fracturing of samples. To freeze fracture the samples, biopsies were placed in a cryo bag (2 per sample) and dipped in liquid nitrogen, then placed in cryoprep (setting 4). The sample bag was taken out and dipped back into nitrogen. A flattened disk was removed and placed into corresponding 2 ml tubes with TRIZOL. The disk was kept frozen in the TRIZOL. The tube was closed and snap-frozen, and the whole tube was placed in liquid nitrogen. After repeating the process with all the samples, samples were placed into boxes and stored at −80° C. until needed for further processing.

Before thawing the samples, a PLG Heavy Tube was prepared by pre-spinning at 12,000 rpm for 2 minutes. Frozen round bottom tubes containing samples were thawed. The samples were bead-beat for 3 minutes at 3,000 rpm. Samples were then centrifuged for 10 minutes at 12,000 rpm. During this time, tubes were set up containing 200 µl chloroform in 1.5 ml tubes. The TRIZOL supernatant was taken and added to a tube containing chloroform, then vortexed for 15 seconds. A total of 1.2 ml of supernatant and chloroform was added to the PLG Tube. Samples were centrifuged for 10 minutes at 12,000 rpm. The aqueous phase was removed from the PLG tube to 2 ml deep wells, and each set of 24 was collected in the same plate for storing at 4° C. between additions.

Next, a Magmax magnetic bead RNA extraction was performed. The Deepwell plates containing the aqueous phase were thawed. For mRNA extraction, procedures known in the art and/or recommended by suppliers of mRNA extraction reagents were followed to obtain isolated mRNA. Once plates were setup for the Magmax, the appropriate protocol was selected, and the plates were loaded. A 35-minute run cycle was performed and the plates were removed. The elution plate was sealed with foil and a lid was placed over the foil. RNA was stored at −80° C. until needed.

A nanodrop-quantification and purity assessment was performed on the isolated mRNA using an EPOCH plate reader and Gen5 software. A reading was taken using 3 µl of sample and the software automatically exported the data to Excel.

While the above Example utilized specific methods to process and analyze mRNA, a person of ordinary skill in the art will recognize that any similar procedures may be utilized.

RNA Quantification Gel Protocol

An RNA quantification gel was prepared using Agilent Chip RNA-Nano. Reagents were allowed to warm up to room temperature for 10 minutes. 550 µl Agilent Red (Gel) was transferred into a filter column and centrifuged for 10 minutes at 1,500 g at room temperature. Agilent Blue (Dye) was vortexed for 10 seconds. 65 µl of filtered gel was transferred into a tube, 1 µl of Agilent Blue (Dye) was added, and the tube was centrifuged at 13,000 g for 10 minutes. Next, an Agilent chip was loaded into the priming station along with 9 µl of Gel-Dye Mix. The priming station was closed for 30 seconds and the plunger was subsequently pulled. The priming station was loaded with 9 µl of Gel-Dye mix into the remaining 2 G-Wells. The wells were loaded with the following: 5 µl of Agilent Green in each well, 1 µl of Agilent Yellow (Nano Ladder) to the ladder well and 1 µl of sample to the sample wells. Vortexing in a chip shaker was performed for 1 minute, after which time an Agilent Analyzer was used according to the manufacturer's specifications.

cDNA Synthesis cDNA was synthesized from the mRNA samples. cDNA reactions were prepared in a 0.2 ml PCR strip tube with mastermix first, then sample and water. Tubes were placed in a thermal cycler and a cDNA thermal cycling protocol recommended by the manufacturer was followed. Samples were stored at −20° C. until need needed.

PCR Setup

Expression levels of inflammation marker genes were determined by PCR using Quanta Perfecta Sybr green master mix with ROX. PCR plates were number coded for the project. All plates came pre-plated with the primers needed for PCR. Reagents were mixed, and the reaction mixture was aliquoted across the plates with 20 µl per well in room temperature plates. Plates were set up in a 12×8 pattern—8 samples down the plate and 12 genes across. PCR analysis utilized StepOne software.

Example 4

Inducers of Inflammation in Ex Vivo Skin Samples

Various known inducers of inflammation, such as pro-inflammatory cytokines, were tested using the ex vivo skin model system. Various pro-inflammatory cytokines, including IL-17, IL-22, IL-1β, and combination thereof, were shown to induce inflammation in ex vivo skin samples.

Ex vivo skin samples were obtained, prepared and cultured as described herein. Various schedules of inflammation inducer exposure were explored to identify a schedule that would lead to an inflammatory state sustained for a period (e.g., 4-6 days) sufficient to verify the presence, and modulation of, regulable inflammation, because it typically takes 4-6 days for inflammation to normalize. These studies led to the addition of inflammation inducer on each of the first four days of culturing the human ex vivo skin samples. Accordingly, the samples were either contacted with IL-1β (10 ng/ml) for four days or left untreated. TNF-α expression and IL-6 expression was monitored on each day of the eight-day experiment by determining the amount of biomarker present in the media.

FIGS. 1 and 2 illustrate the results of exposing the ex vivo skin sample to IL-1β at 10 ng/mL. As seen in FIG. 1, IL-1β induced an increase in TNF-α expression of from about 65 pg/ml to about 120 pg/ml, consistent with the role of IL-1β as an inducer of inflammation. As seen in FIG. 2, IL-1β administered at 10 ng/ml over the first four days of the eight-day experiment, resulted in an increase in IL-6 expression from an average of about 8.2 ng/ml to as high as 12.3 ng/ml, which corresponds to an inflammatory response.

Another study of the effect of IL-1β was performed on ex vivo skin samples obtained, prepared and cultured as described herein but analyzed for gene expression changes instead of modulation of cytokine secretion. Skin samples were exposed to 100 pg/ml of IL-1β and the fold-change in expression of three inflammation marker genes, IL-8, IL-6 and TNF-α, were determined over a time course of 10 days.

The results of this study are illustrated in FIG. 3, and as illustrated in FIG. 3, up-regulation of gene expression levels of 3 key inflammatory markers confirms the inflammatory effect of IL-1β in the present ex vivo skin model. The fold-change for IL-8 was 3.28 after 1 day or 24 hours, 2.58 after 2 days, 7.88 after 3 days, 5.47 after 4 days, 2.42 after 6 days and 9.02 after 10 days. For TNF-α, the fold-change in expression was −1.21 after 1 day, 1.34 after 2 days, 1.37 after 3 days, 2.67 after 4 days, −1.29 after 6 days, and 1.19 after 10 days.

The studies reported in this Example establish that IL-1β functions as an inducer of inflammation in the ex vivo skin model, although the level of induction as revealed by inflammation marker gene expression was found to vary over time. Notwithstanding this variance, IL-1β remains a suitable inducer of inflammation in the methods herein because studies disclosed the Examples below demonstrate that some inhibitors of inflammation may be specific for endogenous skin inflammation (e.g., apigenin) and some inhibitors are specific for induced inflammation (e.g., ZPT), while other inhibitors function well at inhibiting both types of inflammation (e.g., clobetasol). Given that there is more than one type of inflammation demonstrated herein, and knowing that inflammation can arise in a number of ways from differing causes, it is contemplated that IL-1β will be particularly useful in methods for identifying modulators of inflammation that are selective for skin inflammation having a particular cause or using a particular pathway for elaborating the inflammatory response.

Example 5

Examination of IL-17 and IL-22 for Use in the Ex Vivo Skin Model System

IL-17 and IL-22 were examined for inflammation-inducing effects in the cells of ex vivo skin samples. Both IL-17 and IL-22 were found to induce inflammation in the ex vivo skin samples, particularly in combination. Additional studies of these cytokines were conducted to more fully understand the effects these molecules were having on the skin cells and to optimize the amounts to use in the disclosed methods for identifying modulators of skin inflammation.

In one assay, ten ng/ml of each of IL-17 and IL-22 was added to ex vivo skin samples obtained, prepared and cultured as described herein. In a second assay, twenty ng/ml of each of IL-17 and IL-22 was added to ex vivo skin samples obtained, prepared and cultured as described herein The fold-regulation in expression of three inflammation marker genes, i.e., IL-8, IL-6 and TNF-α, was determined over a time course of 10 days and compared to an untreated control. The results are illustrated in FIG. 4.

Figures 4, 5:
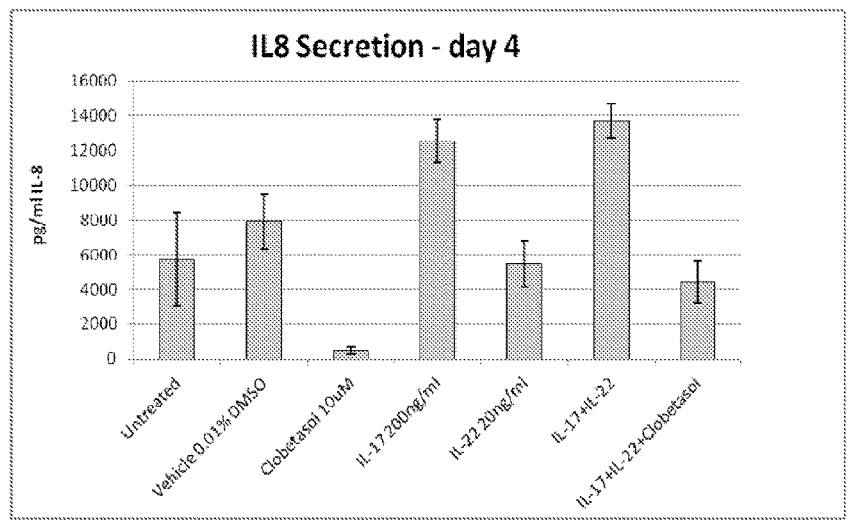
FIG. 4 is an illustration of a response by the ex vivo skin model to an inflammation inducer.
FIG. 5 is an illustration of a response by the ex vivo skin model to an inflammation inducer and an inflammation modulator.

As illustrated in FIG. 4, IL-17 in combination with IL-22 demonstrates appropriate up-regulation of gene expression of key inflammatory markers. The change in fold-regulation after IL-17/IL-22 induction of inflammation was 2.19 for day 1, 3.95 for day 2, 2.81 for day 3, 6.75 for day 4, 5.66 for day 6, and 3.44 for day 10. Fold-change in TNF-α expression levels attributable to IL-17/IL-22 induction of inflammation were −1.03 for day 1, 1.44 for day 2, 1.2 for day 3, 2.30 for day 4, −1.39 for day 6, and −1.99 for day 10. The experiment was repeated with 20 ng/ml for each of IL-17 and IL-22 to induce inflammation. Results for IL-8 expression, in terms of fold-regulation in expression relative to an untreated control, were 4.28 for day 1, 4.32 for day 2, 5.01 for day 3, 13.73 for day 4, 4.43 for day 6 and 6.01 for day 10. For TNF-α, the fold-change in expression over time was −1.17 for day 1, 1.51 for day 2, 1.73 for day 3, 2.06 for day 4, −2.06 for day 6, and −3.73 for day 10. Interestingly, the combined IL-17/IL-22 inflammation inducer had a strong up-regulating effect on IL-8, but a significantly weaker effect on TNF-α. Notable is the apparent plateau in IL-8 up-regulation (and TNF-α expression levels) within the 10-day time course of the experiment, indicating that the ex vivo skin samples remain subject to regulation of the inflammatory process even in the presence of exogenous inducers of inflammation.

An assessment of inflammation inducers, applied alone or in combination to the ex vivo skin model, was conducted to determine the effect on inflammation marker gene expression (IL-8). Ex vivo skin samples were obtained, prepared and cultured as described elsewhere herein and results were obtained at day 4. The treated samples were compared to untreated ex vivo skin samples or ex vivo skin samples treated with only a DMSO vehicle. The results of this experiment are illustrated in FIG. 5.

As illustrated in FIG. 5, secretion of IL-8 into the media by the ex vivo tissue is increased with IL-17 and IL-17+IL-22 treatment. The anti-inflammatory steroid, clobetasol appropriately inhibits both endogenous (wound driven) and induced (cytokine driven) inflammation. An untreated ex vivo skin sample produced about 5,800 pg/ml, while a skin sample exposed to vehicle in the form of 0.01% DMSO expressed about 8,000 pg/ml IL-8. Contacting an otherwise untreated sample with 10 μM clobetasol led to expression of about 400 pg/ml IL-8. A skin sample exposed to 200 ng/ml IL-17 expressed about 12,500 pg/ml IL-8, while a sample exposed only to 20 ng/ml IL-22 expressed about 5,500 pg/ml IL-8. Exposing a skin sample to a combined 200 ng/ml IL-17 and 20 ng/ml IL-22 yielded IL-8 expression of about 13,600 pg/ml. Another skin sample exposed to 200 ng/ml IL-17 and 20 ng/ml IL-22 was also exposed to 10 μM clobetasol and expressed about 4,400 pg/ml IL-8. FIG. 5 also illustrates that while the bulk of inflammation marker gene expression appears to be attributable to IL-17 induction, the combined IL-17/IL-22 induction did lead to an even more pronounced inflammatory response, as measured by the expression levels of the IL-8 inflammation marker gene.

In another experiment, ex vivo skin samples were exposed to one of three concentrations of IL-22, which is known in the art to increase epidermal proliferation and beta-defensin expression levels. A dose-response curve was generated for the expression levels of two inflammation marker genes, i.e., DEFB4 and KRT10, relative to an untreated ex vivo skin sample. The results are illustrated in FIGS. 6 and 7.

Figure 6:
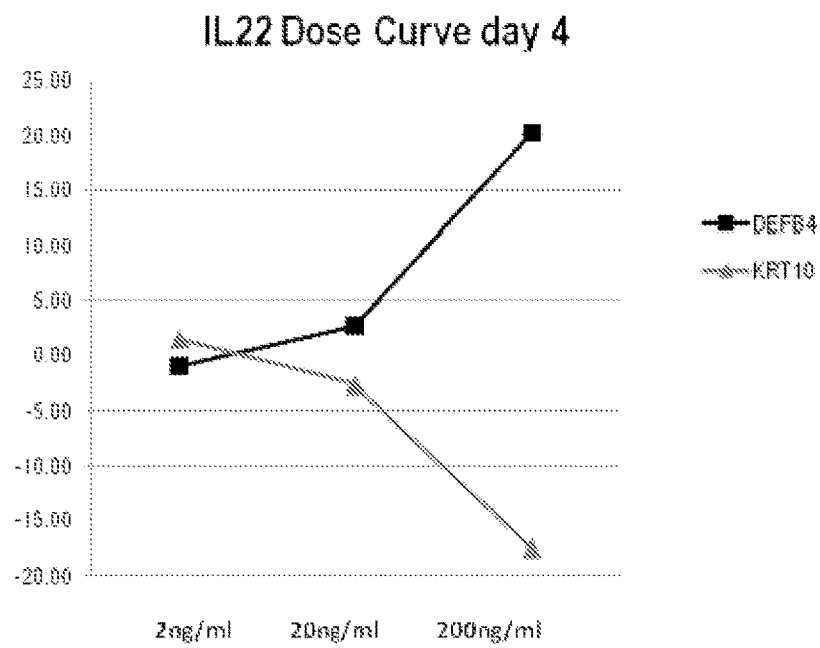
FIG. 6 is an illustration of a response by the ex vivo skin model to an inflammation inducer.

As illustrated in FIG. 6, DEFB4 was expressed at 0.00 in 2 ng/ml IL-22, about 3.00 in 20 ng/ml, and about 20.00 in 200 ng/ml, establishing a positive correlation between IL-22 concentration and DEFB4 expression level. For KRT10, the fold-expression level was about 0.00 for 2 ng/ml IL-22, about −3.00 for 20 ng/ml IL-22 and about −18.00 for 200 ng/ml IL-22. Thus, treatment of the ex vivo skin model appropriately up-regulates gene expression of the anti-bacterial defense protein DEFB4 (beta defensin) and down-regulates of Kerratin 10 gene expression (a marker of differentiation), which is known to be an indicator of epidermal proliferation.

Figure 7:
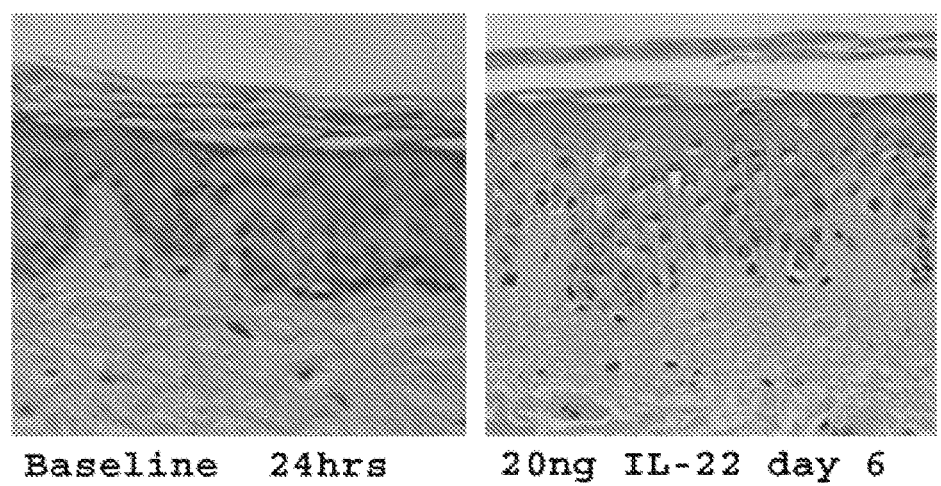
FIG. 7 shows micrographs of samples of ex vivo human skin obtained for histological analysis.

FIG. 7 shows micrographs of two samples obtained for histological analysis. The first sample was analyzed 24 hours after being collected (i.e., biopsied) from an untreated ex vivo skin sample, and the second sample was collected (i.e., biopsied) from an ex vivo skin sample six days after the skin sample was treated with IL-22 at 20 ng/mL. As can be seen in FIG. 7, the second sample clearly exhibits a proliferative basal layer relative to the first sample. Thus, histological analysis shows that IL-22 affects ex vivo skin cell proliferation Expanding the above analysis to look at three additional inflammation marker genes showed that the combination of IL-17 (200 ng/ml) and IL-22 (20 ng/ml) consistently induced an upregulation of the marker genes, which included S100A7, IL-6 and DEFB4 in addition to IL-8. Also consistent was the effect of 10 μM clobetasol in inhibiting inflammation, as measured by a reduction in marker gene expression. In particular, S100A7 was induced about 34-fold relative to untreated skin samples, with clobetasol leading to about 26-fold increase in expression relative to the untreated control. For IL-8, induction was about 16-fold and clobetasol reduced that to about 3-fold. For IL-6, induction was about 6-fold and clobetasol inhibited that value to about 0.3-fold relative to control values. For DEFB4, induction was about 800-fold and clobetasol reduced that increase to about 200-fold relative to controls. Thus, the IL-17/IL-22-induced inflammatory response was detected by measuring expression of each of four inflammation marker genes, i.e., IL-8, IL-6, S100A7 and DEFB4. Additionally, the experiment showed that the inhibition of inflammation resulting from clobetasol administration could be detected by measuring expression levels of each of these four inflammation marker genes.

The experiment was expanded again to include nine inflammation marker genes. As with the preceding experiment and other experiments described herein, ex vivo skin samples were obtained, prepared and cultured as described herein. Each skin sample was then exposed to IL-17 (200 ng/ml) and IL-22 (20 ng/ml) as a combined inducer of the inflammatory response, with some samples, but not others, further exposed to 10 μM clobetasol as an inhibitor of inflammation. The effect of these conditions on each of nine inflammation marker genes was assessed relative to an untreated control. The results are illustrated in FIG. 8 as fold-regulation data.

Figures 8, 9:
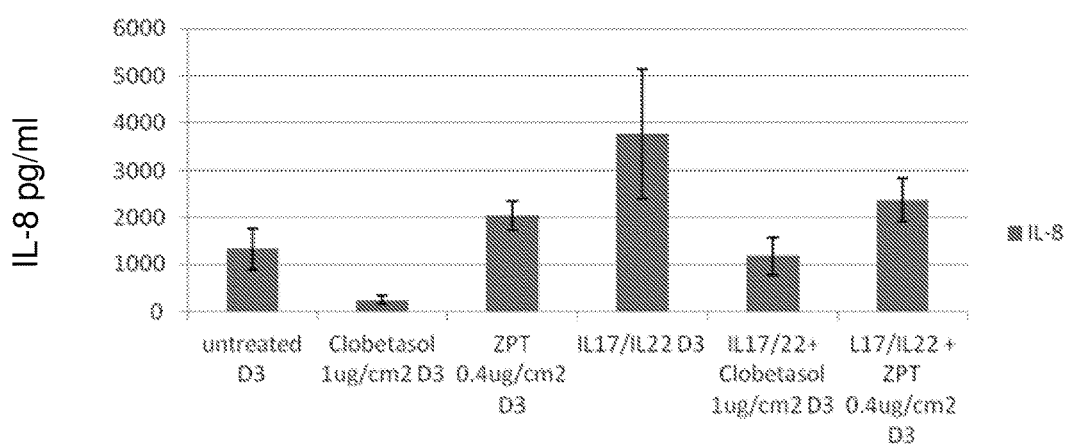
FIG. 8 is an illustration of a response by the ex vivo skin model to an inflammation inducer and an inflammation modulator.
FIG. 9 is an illustration of responses by the ex vivo skin model to inflammation inducers and inflammation modulators.

As illustrated in FIG. 8, the anti-inflammatory steroid, clobetasol, appropriately inhibits gene expression of key inflammatory markers in both the endogenous and IL-17+IL-22 driven inflammation.

Another experiment was designed to identify optimal inflammation inducer concentrations. The experiment resulted in the production of concentration curves that were constructed based on ex vivo skin tissue samples contacted with IL-17, IL-22, or a combination of IL-17 and IL-22 at varying concentrations, followed by measuring gene expression of a battery of markers of inflammation. The ex vivo skin tissue samples were obtained, prepared and cultured as described herein. These ex vivo skin samples were then incubated with the aforementioned inducers of inflammation and expression levels of the markers of inflammation were determined and compared to control ex vivo skin tissue samples that were not contacted with inducers of inflammation. The results are provided in Table 1, below.

TABLE 1

| 96 hours | IL-17 (2 ng/ml) | IL-17 (20 ng/ml) | IL-17 (200 ng/ml) | IL-22 (2 ng/ml) | IL-22 (20 ng/ml) | IL-22 (200 ng/ml) | IL-17 + IL-22 (2/2 ng/ml) |
|---|---|---|---|---|---|---|---|
| S100A7 | 1.38 | 1.50* | 4.44* | 1.02 | 2.04* | 3021* | −1.42* |
| IL-8 | 1.64 | 1.69* | 2.39* | 1.71* | 1.43 | 1.72* | 2.22* |
| IL-6 | 1.65* | 1.53* | 1.94* | 1.35 | 1.30 | 1.31 | 1.55* |
| DEFB4 | 1.08 | 1.79* | 21.22* | −1.03 | 2.69* | 20.23* | 1.36 |
| KRT10 | −1.37 | −1.93* | −1.56* | 1.40 | −2.69* | −17.54* | 1.01 |
| KRT6A | −1.29 | −1.30 | −1.12 | −1.16 | 1.32 | 1.08 | −1.06 |
| TNF-α | 1.67* | 1.75* | 1.65* | 1.95* | 1.56* | 1.33* | 2.13* |
| FLG | 1.11 | −1.88* | −1.15 | 1.28 | −10.55* | −13.37* | 1.23 |
| CALML5 | 1.09 | −1.10 | 1.89* | 1.17* | −2.29* | −4.61* | −1.15 |

| 96 hours | IL-17 + IL-22 (2/20 ng/ml) | IL-17 + IL-22 (2/200 ng/ml) | IL-17 + IL-22 (20/2 ng/ml) | IL-17 + IL-22 (20/20 ng/ml) | IL-17 + IL-22 (20/200 ng/ml) | IL-17 + IL-22 (200/2 ng/ml) | IL-17 + IL-22 (200/20 ng/ml) |
|---|---|---|---|---|---|---|---|
| S100A7 | 1.72 | 3.41* | 1.74* | 4.11* | 8.91* | 4.07* | 7.92* |
| IL-8 | 1.65 | 2.49* | 3.35* | 2.40* | 7.19* | 3.57* | 3.52* |
| IL-6 | 1.25 | 1.74* | 1.89* | 2.11* | 2.29* | 3.31* | 2.45* |
| DEFB4 | 2.46 | 17.28* | 2.43 | 12.88* | 150.72* | 30.95* | 296.66* |
| KRT10 | −2.05 | −15.80. | −1.65. | −4.02* | −107.88* | −3.15* | −91.91* |
| KRT6A | 1.26 | 1.13 | −1.34. | 1.18 | −1.16 | −1.18 | −1.48* |
| TNF-α | 1.28 | 1.15 | 2.21* | 1.51* | −1.19 | 1.31* | 1.13 |
| FLG | −11.10 | −13.52* | −1.33 | −12.73* | −28.06* | −1.44* | −19.68* |
| CALML5 | −2.46 | −4.82* | −1.25* | −2.36* | −10.37* | 1.60* | −7.16* |

*p ≤ 0.05

The results indicated that the level of IL-17, IL-22, or IL-17/IL-22 could be varied significantly (e.g., by ten-fold or more) and still generate significant up-regulation of IL-6 and IL-8. For example, IL-17 induced expression of S100A7 in a range of 2 ng/ml to 200 ng/ml.

This Example demonstrates that the concentrations of IL-17 and IL-22 used in the methods herein may be selected depending on the experimental need. For example, suitable concentrations of IL-17 and/or IL-22, used individually or in combination, may be between 2-200 ng/ml each.

Example 6

Inhibitors of Inflammation—Endogenous or Induced Inflammation in Ex Vivo Skin Samples Disclosed herein is data showing that clobetasol inhibits endogenous and induced inflammation in ex vivo skin samples, and it does not destroy the ability of the skin tissues and cells to regulate the inflammatory response. Experiments were thus conducted to compare the effects of other known inhibitors of inflammation on inflamed ex vivo skin samples.

Ex vivo skin samples were obtained, prepared and cultured as described elsewhere herein. Individual ex vivo skin samples were then either left untreated, resulting in endogenous inflammation, or exposed to a combination of IL-17 and IL-22 as an inducer of inflammation. Expression levels were determined on day 3. The results of this experiment are illustrated in FIG. 9.

As can be seen in FIG. 9, An untreated skin sample exposed to topical application of clobetasol at 1 μg/cm² skin surface led to a reduction in expression of the IL-8 inflammation marker gene from about 1,200 pg/ml to about 200 pg/ml. Substituting 0.4 μg/cm² zinc pyrithione (ZPT) for the clobetasol led to about 2,000 pg/ml IL-8 expression. Skin samples subjected to IL-17/IL-22-induced inflammation expressed about 3,800 pg/ml IL-8 expression, while further addition of 1 pg/cm² topical clobetasol reduced IL-8 expression to about 1,100 pg/cm² and, separately, addition of 0.4 μg/cm² topical ZPT yielded about 2,300 pg/ml IL-8. These results demonstrate that clobetasol inhibits IL-8 secretion with and without IL-17+IL-22. ZPT reduces secretion in the induced inflammation (11-17+IL-22) model but not the endogenous with 3 days of treatment. Thus, the ex vivo skin model is capable of differentiating between different mechanisms of inhibition of inflammation.

The effect of clobetasol on an induced inflammatory response of ex vivo skin samples was also assessed by measuring the expression of inflammation marker genes IL-6, S1100A7 and DEFB4 in addition to IL-8. The ex vivo skin samples were obtained, prepared and cultured as described above. Inflammation was induced by delivering a combination of IL-17 (200 ng/ml) and IL-22 (20 ng/ml). The effect of 10 μM clobetasol on the induced inflammatory response was assessed by measuring the expression levels of IL-8, IL-6, S100A7 and DEFB4 as inflammation marker genes. Results showed that, for each of the four inflammation marker genes, clobetasol significantly reduced expression levels seen in the inflammatory state induced by the IL-17/IL-22 combination. For IL-6, the inhibition was so strong that the expression level in the presence of the inducers and clobetasol was lower than the IL-6 expression level in untreated skin cells (i.e., cells not exposed to the inducer combination or the inhibitor). The results of this experiment are illustrated in FIG. 8.

Another study using clobetasol as a control (i.e., a positive control inhibiting the inflammatory response) was conducted using human ex vivo skin samples obtained from different donors to assess the ability to regulate the inflammatory response in ex vivo skin samples from different donors. Ex vivo skin samples from five different human donors were prepared as described in Example 1 and cultured as described in Example 2. The expression levels of IL-8 and IL-6, two inflammation marker genes, were measured in endogenously inflamed skin samples and the expression levels for these inflammation marker genes were compared to their levels after treatment of skin samples with 10 µM clobetasol. The fold-regulation in secretion of IL-8 and IL-6 for each of five skin donors was measured. The results are illustrated in FIG. 10.

As illustrated in FIG. 10, expression of IL-8 in each of the five ex vivo skin samples exposed to 10 µM clobetasol were −2.72, −2.72, −3.68, −3.89, and −1.76. Expression of IL-6 in each of the five ex vivo skin samples exposed to 10 µM clobetasol were −3.28, −3.55, −8.69, −5.70, and −2.20. Thus, 10 µM clobetasol reliably induced a statistically significant inhibition of each of two inflammation marker genes, IL-8 and IL-6, in ex vivo skin samples from five different donors.

Similarly, FIG. 11 illustrates the results of treating human ex vivo skin samples obtained from 5 different donors with 20 ng/ml IL-17 and 20 ng/ml IL-22. As can be seen in FIG. 11, treatment with IL-17+1L-22 demonstrated similar fold-regulation of an extended set of biomarker genes in ex vivo skin samples from different donors.

Investigations to date have led to the expectation that clobetasol inhibits the inflammatory response and IL-17+ IL-22 drives inflammatory response in more than 80% of human ex vivo skin samples when varying the skin source, or donor. Clobetasol is a reliable control for identifying modulators of the inflammatory response and IL-17+IL-22 is a reliable control for inducing inflammation in human ex vivo skin samples, regardless of source. In this regard, the ex vivo skin samples continue to behave as in vivo skin. Although clobetasol and IL-17+IL-22 are not the only useful positive controls, the data show that both are widely effective across donor materials in functioning as a control for the ability to inhibit or drive inflammation in a given ex vivo tissue sample. Such controls are important for using the present model as an anti-inflammatory screen. The data further contribute to the robust nature of the human ex vivo skin model and the method of identifying modulators of skin inflammation that makes use of the model in that skin samples from different donors are largely regulable, and clobetasol is at least one inhibitory positive control that functions across a wide range of donor materials. 11-17+ IL-22 is at least one driver of inflammation that functions across a range of donor materials. With the identification of these useful controls, the methods of identifying modulators of inflammation can be practiced on any human skin sample, confident that any rare sample not exhibiting the expected endogenous and/or induced inflammatory response, and/or not responding properly to the control (e.g., inhibitor of skin inflammation) can be readily identified and any results obtained using such samples addressed with caution.

Another study looked at selenium sulfide as an additional inhibitor of inflammation, and examined the effects of this inhibitor relative to clobetasol on reducing IL-8 secretion. Separate inflamed skin samples were exposed to selenium sulfide at concentrations of 0.04 µM, 0.2 µM, 1 µM, 5 µM and 25 µM, and one skin sample was exposed to 10 µM clobetasol. The results are illustrated in FIG. 12.

As illustrated in FIG. 12, selenium sulfide demonstrates a dose response of inhibition of the endogenous inflammation in the ex vivo skin samples. In particular, selenium sulfide concentrations of 0.04-25 µM resulted in decreased secretion levels of IL-8. These results provide a basis for relying on S100A7, IL-8 and IL-6 as inflammation markers with selenium sulfide as an inhibitor of inflammation.

To broaden the base of suitable inflammation inhibitors still further, an experiment was conducted to assess the effects of 1,10-phenanthroline relative to the now-established inhibitory effects of clobetasol. Ex vivo skin samples were obtained, processed and cultured as described above. Using IL-8 as the inflammation marker gene, the effect on expression of endogenous inflammation in a skin sample was compared to the expression levels in the presence of separate topical applications of 10 µM clobetasol or 1.2 µg/ml 1,10-phenanthroline as inflammation inhibitors. The results of this experiment are illustrated in FIGS. 13A and 13B.

As can be seen from FIG. 13A, results at day 3 showed that IL-8 was secreted at about 2,600 pg/ml in an endogenously inflamed skin sample, while addition of clobetasol inhibited IL-8 secretion to about 300 pg/ml and 1,10 phenanthroline inhibited IL-8 secretion to about 900 pg/ml. Thus, 1,10-phenanthroline and clobetasol functioned to inhibit secretion of the IL-8, although 1,10-phenanthroline may have functioned as a weaker inhibitor than clobetasol. The result establishes that 1,10-phenanthroline, like clobetasol, apigenin and other inhibitors, inhibits endogenous inflammation in ex vivo skin samples.

FIG. 13B illustrates the affect of clobetasol and 1,10-phenanthroline on the gene expression of IL-8, IL-6, S100A7 and DEFB4. As can be seen in FIG. 13B, the results at day 3 show that 10 µM clobetasol inhibited expression of IL-8, IL-6 and S100A7 and 1.2 µg/ml 1,10-phenanthroline expression of IL-8, IL-6, S100A7 and DEFB4. Thus, 1,10 phenanthroline and clobetasol, when applied topically for 72 hours, can suppress inflammation in the ex vivo skin model, which suggests that the present model may be used for media- and topically-applied actives.

Thus, clobetasol, 1,10-phenanthroline, and other inhibitors of inflammation disclosed herein, such as apigenin, ZPT, selenium sulfide, arlatone, betamethasone, ketoprofen and hydrocortisone, are contemplated for use as positive controls in methods according to the disclosure, with the compounds functioning as positive controls by inhibiting inflammation in ex vivo skin samples, as measured by expression and/or secretion levels of at least one inflammation marker gene identified herein (e.g., IL-8, IL-6, S100A7, DEFB4, KRT10, KRT6A, TNF-α, FLG, CALML5, ceramide synthase 3, and HMGCR).

Example 7

Inhibitors of Endogenous and Induced Inflammation

The preceding Example established, among other things, that clobetasol functioned well as an inhibitor of endogenous and induced inflammation in the ex vivo skin model. Experiments were designed to characterize the types of inflammation inhibited by other inflammation inhibitors disclosed herein. At the outset, it was unclear whether a given inhibitor would inhibit endogenous inflammation, induced inflammation, or both types of inflammation as the responses were elaborated in the ex vivo skin model. This knowledge would assist in the design of methods for identifying modulators of inflammation in that any mismatch between inflammation type and inhibitor could be avoided. Additionally, the information would facilitate more tailored approaches to the identification of modulators effective against particular types of inflammation.

Skin samples were obtained, prepared and cultured as described above. IL-8 was used as the inflammation marker and skin samples were incubated for four days before determining expression levels. The results of this experiment are illustrated in FIG. 14.

Figures 14, 15:
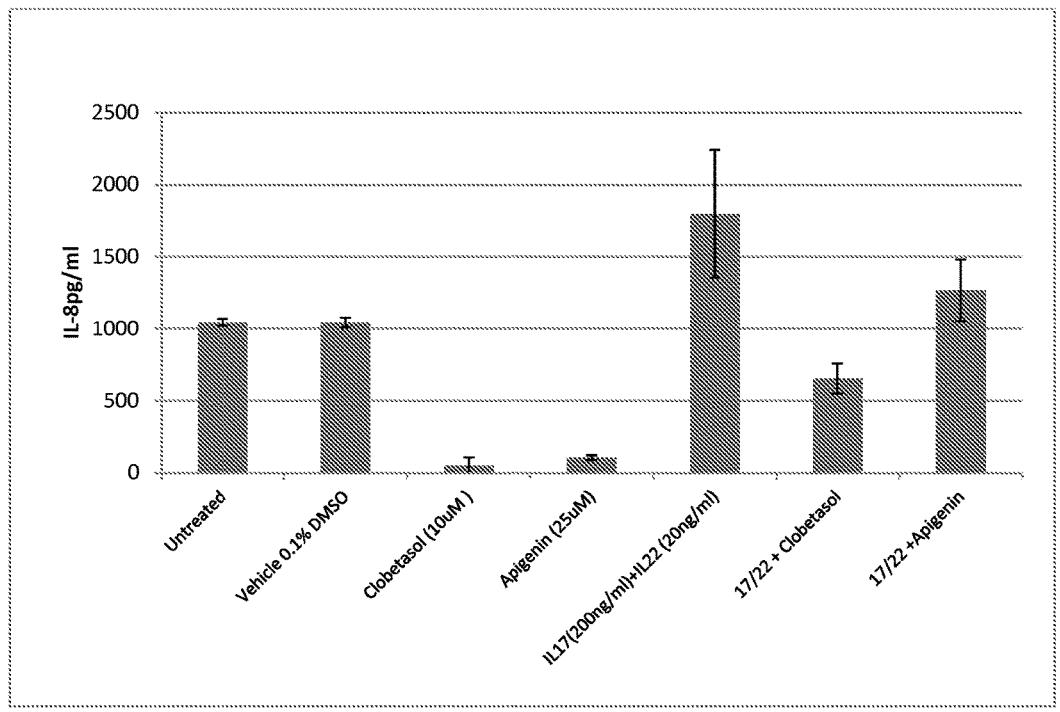
FIG. 14 is an illustration of responses by the ex vivo skin model to inflammation inducers and inflammation modulators.
FIG. 15 is an illustration of responses by the ex vivo skin model to inflammation modulators.

As can be seen in FIG. 14, endogenously inflamed skin samples (i.e., untreated) expressed 1045 pg/ml IL-8 at day 4. Other individual skin samples were exposed to IL-17 (200 ng/ml)+IL-22 (20 ng/ml) to induce inflammation and expressed 1798 pg/ml IL-8 at day 4. Other skin samples were not induced, but were exposed to an inflammation inhibitor, with 25 µM apigenin leading to 106 pg/ml IL-8 (day 4), (day 4), or 10 µM clobetasol expressing 50 pg/ml IL-8 (day 4). Still other skin samples were induced to elaborate an inflammatory response by IL-17 (200 ng/ml)/IL-22 (20 ng/ml) administration, and separate induced skin samples were then inhibited with any one of 25 µM apigenin [1276 pg/ml IL-8], or 10 µM clobetasol [65 pg/ml IL-8]. The values provided in square brackets for each condition are the results obtained on day 4 for IL-8 expression. The results confirm that clobetasol functions effectively as an inhibitor of both endogenous and induced inflammation in ex vivo skin samples. Apigenin functions effectively in inhibiting endogenous inflammation, but it does not appear to function effectively to inhibit induced inflammation, providing a tool to selectively inhibit endogenous inflammation. Conversely, it was previously demonstrated that ZPT did not significantly inhibit endogenous inflammation but did inhibit IL-17, IL-22 induced inflammation, which suggests that the present ex vivo skin model can provide a tool for preferentially inhibiting induced inflammatory responses in skin.

The experiments described above involving differing types of inflammation (endogenous and induced), various inhibitors of inflammation, and various inflammation marker genes provided a sound base for concluding that the ex vivo skin model was useful in performing methods of identifying modulators of skin inflammation. That conviction led to the design of the experiment described in the next Example, in which the number of inflammation inhibitors and the number of inflammation marker genes were both increased to assess the strength of the ex vivo skin model and its use in methods of identifying modulators of skin inflammation.

Example 8

Inflammation Marker Genes

The methods of identifying modulators of skin inflammation, and the use of the ex vivo skin model to identify such modulators, depends on the ability to monitor inflammatory responses in skin cells and tissues. Disclosed herein is the use of expression levels for selected genes found to be responsive to the inflammatory state, i.e., genes having expression levels that are detectably different in a cell within an inflamed tissue from the expression in that same cell, or more realistically a cell of the same type, that is not part of an inflamed tissue. Based on experiments disclosed herein, the following set of inflammation marker genes has been identified: IL-8, IL-6, S100A7, DEFB4, KRT10, KRT6A, TNF-α, FLG, CALML5, ceramide synthase 3, and HMGCR. The expression levels may involve a measure of transcribed RNA, total protein production, or at least one protein activity.

An experiment was conducted to examine the expression level of IL-8, IL-6, S100A7, DEFB4, KRT10, KRT6A, FLG and CALML5 in endogenously inflamed ex vivo skin samples exposed to one of five inflammation inhibitors. The inflammation inhibitors were 10 µM clobetasol, 0.6 nM betamethasone, 0.08 µM hydrocortisone, 30 µM ketoprofen, and 35 µM arlatone. Results showed that all inflammation inhibitors inhibited the expression of IL-8, IL-6, DEFB4, KRT6A and TNF-α. In contrast, all but 1 induced expression of KRT10. For the remaining inflammation marker genes, the inhibitor effects varied but the trend amongst the steroidal group was consistent. While clobetasol inhibited S100A7 expression, the other four inhibitors induced expression of this marker gene. For FLG, ketoprofen and arlatone slightly inhibited expression while the remaining inhibitors reduced expression. For CALML5, all inhibitors except ketoprofen induced expression, with ketoprofen slightly inhibiting expression. The data were analyzed and led to a rank ordering of inflammation inhibitors based on IL-8 and IL-6 inhibition levels in which clobetasol was the most effective inhibitor, followed by betamethasone, hydrocortisone, ketoprofen and arlatone. In terms of the fold-change in expression of the inflammation marker genes relative to an untreated ex vivo skin sample, the results are illustrated in FIG. 15.

As illustrated in FIG. 15, the present ex vivo skin model is capable of rank ordering efficacy of various steroidal and non-steroidal anti-inflammatory compounds. The strongest anti-inflammatory compound, clobetasol, shows the greatest reduction in the three markers (i.e., IL-6, IL-8, and TNFα), followed by less robust steroids betamethasone, hydrocortisone, and ketoprofen. Last is arletone, which shows some inhibition.

This study shows that reliance on an over-simplified assay system, much like over-reliance on in vitro assays and other approaches to physiological measurements that rely on systems well-removed from in vivo conditions, can produce false or misleading results. Use of more than one gene from the panel of inflammation marker genes (i.e., IL-8, IL-6, S100A7, DEFB4, KRT10, KRT6A, TNF-α, FLG, CALML5, ceramide synthase 3, and HMGCR) produces a robust assay design that will minimize false results or anomalies, leading to increased confidence in the results despite the efficient and cost-effective approach that has been developed. Further strengthening the methods according to the disclosure is the use of one or more of several known inhibitors as positive controls, such as clobetasol, 1,10-phenanthroline, apigenin, ZPT, selenium sulfide, arlatone, betamethasone, ketoprofen and hydrocortisone. In using positive controls, the methods of the disclosure provide a benchmark by which to judge the performance of candidate modulators, and the use of more than one positive control is contemplated as a means of identifying modulators that may affect the expression of one gene differently than a particular positive control (i.e., known inflammation inhibitor).

Example 9

Use of Lipid Metabolism Genes as Inflammation Marker Genes

Genes involved in lipid metabolism were also examined to determine if they might be useful markers for skin inflammation in the ex vivo skin model system. Three of the inflammation inducers disclosed herein, i.e., IL-17, IL-22 and IL-1β, were used to induce inflammation in ex vivo skin samples and the expression levels of two lipid metabolism genes were measured over a 10-day time course.

Figure 16A:
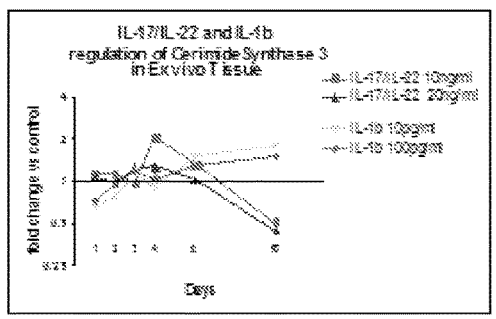
FIGS. 16A and 16B are illustrations of responses by the ex vivo skin model to inflammation inducers.

Ex vivo skin samples were obtained, prepared and cultured as described herein. Expression levels of ceramide synthase 3 and HMG Coenzyme A Receptor (HMGCR) were measured at days 1, 2, 3, 4, 6 and 10. Ex vivo skin samples were induced to elaborate an inflammatory response by administration of either a combination of IL-17/IL-22 or delivering IL-1β. For ceramide synthase 3 expression studies, 10 ng/ml of each of IL-17 and IL22 were used in one experiment, and 20 ng/ml of each of IL-17 and IL-22 were used in a second experiment. IL-1β concentrations used for induction of inflammation were 10 pg/ml and 100 pg/ml in separate experiments. The results of the ceramide synthase 3 experiments are illustrated in FIG. 16A. As can be seen in FIG. 16A, induction with IL-17/IL-22 produced an upregulation in expression of ceramide synthase 3 from about days 3-7, followed by a down-regulation of expression thereafter, resulting in a down-regulation of about 0.5 fold relative to untreated control at day 10, with a slightly greater down-regulation resulting from use of 20 ng/ml concentrations of each inducer. In contrast, IL-1β induction led to relatively flat expression levels for ceramide synthase 3 until about day 3, at which point a gradual and progressive up-regulation of gene expression occurred, culminating in about a 1.5-fold increase in expression at day 10, for both 10 pg/ml and 100 pg/ml IL-1β. Although similar, a detectably greater up-regulation of ceramide synthase 3 expression occurred in response to 10 pg/ml IL-1β, relative to expression induced by 100 pg/ml IL-1β.

Figure 16B:
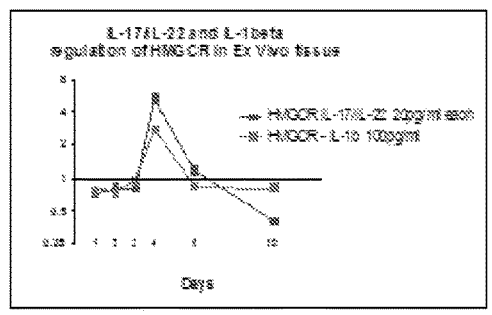

Analogous experiments were performed with HMGCR as the inflammation marker gene. The ex vivo skin samples, manipulated for experimentation as described herein, were exposed to 20 pg/ml of each of IL-17 and IL-22 and HMGCR expression was measured at days 1, 2, 3, 4, 6 and 10 of the 10-day experiment. The results are illustrated in FIG. 16B. As can be seen in FIG. 16B, HMGCR expression was upregulated between days 3-6, peaking at about 6-fold expression relative to untreated controls, but that after day 6, expression was down-regulated, ending at about a 0.45-fold expression level on day 10, relative to untreated controls. Administration of 100 pg/ml IL-1β as inducer produced a similar expression pattern over time, with HMGCR expression up-regulated over days 3-6, but down-regulated thereafter, terminating at about 0.8-fold expression relative to untreated controls. These experiments assessing the merits of using lipid metabolism genes as inflammation marker genes leads to the conclusion that the lipid metabolism genes exhibit repeatable expression patterns when exposed to inflammatory states induced by different inflammation inducers. Although the longer-term expression pattern is one of down-regulation, the consistency of the longer-term down-regulation makes these genes as valuable as marker genes that are consistently up-regulated in inflammatory states. As a result, lipid metabolism genes such as ceramide synthase 3 and HMGCR are suitable inflammation marker genes The various aspects of the disclosure have been described, and embodiments of the disclosure have been presented. In general terms, the ex vivo human skin model and methods of identifying modulators of skin inflammation may comprise one or more of the following (among others): measuring markers of endogenous inflammation and comparing the difference in the level of inflammation after a candidate modulator is applied; applying a positive control to skin and comparing the effects against the effect of an applied candidate modulator; using a positive control that is an inhibitor of inflammation, such as clobetasol, 1,10 phenathroline, arlatone, betamethasone, hydrocortisone, and ketoprofen; applying candidate modulators topically or in media; wherein the marker of inflammation comprises a secreted cytokine, a protective anti-bacterial protein, mRNA corresponding to one or more genes relating to skin inflammation, or a transcriptional profile of genes regulated in response to skin inflammation; using exemplary inflammation marker genes (or their protein expression products) such as IL-6, IL-8, tumor necrosis factor alpha, S100A7, DEFB4, KRT10, KRT6A, FLG, CALML5, ceramide synthase 3, and HMGCR, and combinations thereof; employing methods involving endogenous inflammation wherein expression levels are determined between 96-240 hours after obtaining skin samples or after initiating skin cultures; maintaining skin cultures between 30-40° C. at 50-90% humidity for 3-10 days; using methods in which inflammation is induced, or driven, by inducers such as IL-1β, IL-17 and IL-22; storing skin at 4-10° C.; and using an ex vivo skin model to identify modulators of inflammation useful in cosmetically improving skin, e.g., by reducing redness, blushing, splotchiness, or the like, or in therapeutically treating any of a variety of skin diseases, disorders or conditions, such as eczema, psoriasis, a wound, bacterial exposure, and dandruff.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. In particular, this application claims the benefit of U.S. Provisional Ser. No. 61/683,452, which is incorporated herein by reference in its entirety. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of identifying a modulator of an inflammatory response comprising:
   (a) culturing a first ex vivo human skin sample comprising an epidermal layer and a dermal layer at a temperature of about 37° C. and a humidity of about 50%, wherein the first ex vivo human skin sample is selected from the group consisting of an endogenously inflamed ex vivo human skin sample and an induced inflamed ex vivo human skin sample;
   (b) contacting the first ex vivo human skin sample with a candidate modulator;
   (c) measuring a level of a marker of inflammation in the first ex vivo human skin sample;
   (d) providing a control level for the marker of inflammation; and
   (e) identifying the candidate modulator as a modulator of an inflammatory response when the level of the marker of inflammation in the first ex vivo human skin sample corresponds to a change in inflammation response relative to the control level.

2. The method of claim 1, wherein providing the control level comprises measuring the level of the marker of inflammation of an untreated ex vivo human skin sample.

3. The method according to claim 1, wherein providing the control level comprises contacting a second ex vivo skin sample with a control material and measuring the level of the marker of inflammation.

4. The method according to claim 3, wherein the second ex vivo human skin sample is an induced inflamed ex vivo human skin sample and the control material is at least one of clobetasol and apigenin.

5. The method according to claim 3, wherein the second ex vivo human skin sample is an endogenously inflamed ex vivo human skin sample and the control material is tetrahexyldecyl ascorbate.

6. The method according to claim 1, wherein the ex vivo human skin sample is an induced inflamed ex vivo human skin sample and inflammation is induced in the skin sample by delivering an effective amount of a compound selected from the group consisting of Interleukin (IL)-17, IL-22, IL-1β, and combinations thereof to the ex vivo human skin sample.

7. The method according to claim 6, wherein the inflammation is induced by delivering an effective amount of a combination of IL-17 and IL-22.

8. The method according to claim 6, wherein a constant amount of the compound is delivered during step (b).

9. The method according to claim 1, further comprising repeating steps (a) to (e) with different candidate modulators.

10. The method according to claim 1, wherein steps (a) to (e) comprise a second assay in a tiered screening method and the candidate modulator is selected as a result of performing a first assay of the tiered screen method prior to performing the second assay, wherein the first assay is selected from an enzyme assay, a cell-based culture, an in vitro assay, and an in vivo skin assay.

11. The method according to claim 1, wherein the marker of inflammation is selected from the group consisting of a secreted cytokine, an anti-bacterial protein, a lipid biosynthesis protein and an mRNA corresponding to a gene responsive to skin inflammation.

12. The method according to claim 11, wherein the marker of inflammation is a secreted cytokine selected from the group consisting of IL-6, IL-8, IL-10, IL-12 and tumor necrosis factor alpha (TNFα).

13. The method according to claim 11, wherein the marker of inflammation is an anti-bacterial protein selected from the group consisting of calcium-binding protein A7 (S100A7) and defensin beta 4 (DEFB4).

14. The method according to claim 11, wherein the marker of inflammation is a lipid biosynthesis protein selected from the group consisting of Ceramide Synthase 3 and 3-hydroxy-3-methyl-glutaryl-CoA reductase (HMGCR).

15. The method according to claim 14, wherein step (c) is performed 3-6 days after contacting the ex vivo human skin sample with the candidate modulator and wherein the candidate modulator is identified as a modulator of an inflammatory response when the candidate modulator inhibits expression of the lipid biosynthesis protein.

16. The method according to claim 14, wherein step (c) is performed at least 7 days after contacting the ex vivo human skin sample with the candidate modulator and wherein the candidate modulator is identified as a modulator of an inflammatory response when the candidate modulator increases expression of the lipid biosynthesis protein.

17. The method according to claim 1, wherein the marker of inflammation is an mRNA which encodes for a marker selected from IL6, IL8, IL10, IL12, TNFα, keratin 10 (KRT10), keratin 6A (KRT6A), filaggrin (FLG), calmodulin-like protein 5 (CALML5), S1007A, DEFB4, Ceramide Synthase 3, and HMGCR.

18. The method of claim 1, wherein the level of the marker of inflammation is measured between 96 hours and 240 hours after the ex vivo skin sample is removed from a donor.

19. The method of claim 1, further comprising removing a subcutaneous fat layer from the ex vivo human skin sample.

* * * * *